(12) United States Patent
Baldi et al.

(10) Patent No.: US 8,501,159 B2
(45) Date of Patent: Aug. 6, 2013

(54) MAGNETIC NANOPARTICLES FOR THE APPLICATION IN HYPERTHERMIA, PREPARATION THEREOF AND USE IN CONSTRUCTS HAVING A PHARMACOLOGICAL APPLICATION

(75) Inventors: Giovanni Baldi, Montespertoli (IT); Daniele Bonacchi, Pistoia (IT); Franco Innocenti, Florence (IT); Giada Lorenzi, Pistoia (IT); Marco Bitossi, Montelupo Fiorentino (IT); Paolo Ferruti, Milan (IT); Elisabetta Ranucci, Opera (IT); Alfredo Ricci, Bologna (IT); Mauro Comes Franchini, San Lazzaro di Savena (IT)

(73) Assignee: Colorobbia Italia S.p.A., Sovigliana Vinci (IT)

( * ) Notice: Subject to any disclaimer, the term of this patent is extended or adjusted under 35 U.S.C. 154(b) by 773 days.

(21) Appl. No.: 12/519,682

(22) PCT Filed: Dec. 18, 2007

(86) PCT No.: PCT/EP2007/064143
§ 371 (c)(1),
(2), (4) Date: Jun. 17, 2009

(87) PCT Pub. No.: WO2008/074804
PCT Pub. Date: Jun. 26, 2008

(65) Prior Publication Data
US 2010/0015060 A1 Jan. 21, 2010

(30) Foreign Application Priority Data
Dec. 18, 2006 (IT) ................................. FI2006A0328
Dec. 18, 2006 (IT) ................................. FI2006A0329

(51) Int. Cl.
*A61B 5/055* (2006.01)
(52) U.S. Cl.
USPC ......... 424/9.322; 424/1.11; 424/9.1; 424/9.3; 424/9.32; 424/421
(58) Field of Classification Search
USPC .................. 424/9.1, 9.32, 9.3, 421; 428/402, 428/403, 407, 494; 436/524–528
See application file for complete search history.

(56) References Cited

U.S. PATENT DOCUMENTS

| | | | |
|---|---|---|---|
| 4,101,435 A | 7/1978 | Hasegawa et al. | |
| 4,280,918 A | 7/1981 | Homola et al. | |
| 4,329,241 A | 5/1982 | Massart | |
| 4,452,773 A | 6/1984 | Molday | |
| 4,677,027 A | 6/1987 | Porath et al. | |
| 4,827,945 A | 5/1989 | Groman et al. | |
| 5,160,725 A | 11/1992 | Pilgrimm | |
| 5,427,767 A | 6/1995 | Kresse et al. | |
| 5,545,395 A | 8/1996 | Tournier et al. | |
| 6,255,477 B1 | 7/2001 | Kleiber et al. | |
| 6,423,296 B1 * | 7/2002 | Gunther et al. | 424/9.322 |
| 6,541,039 B1 | 4/2003 | Lesniak et al. | |
| 6,576,221 B1 * | 6/2003 | Kresse et al. | 424/9.322 |
| 6,767,635 B1 * | 7/2004 | Bahr et al. | 428/402 |
| 2006/0182809 A1 | 8/2006 | Blum et al. | |
| 2009/0123507 A1 * | 5/2009 | Ohrlein et al. | 424/421 |

FOREIGN PATENT DOCUMENTS

| | | |
|---|---|---|
| EP | 0272091 A2 | 6/1988 |
| EP | 0272091 A3 | 6/1988 |
| WO | 2004/071386 A2 | 8/2004 |
| WO | 2004/071386 A3 | 8/2004 |
| WO | 2007/077240 A2 | 7/2007 |
| WO | 2007/077240 A3 | 7/2007 |

OTHER PUBLICATIONS

Brigger et al., "Nanoparticles in cancer therapy and diagnosis" Advanced Drug Delivery Reviews 54, 2002, 631-651.
Ferruti et al, "Poly(amido-amine)s: Biomedical Applications" Macromolecular Rapid Communication, Wiley-VCH Verlag GmbH, 2002, 23, No. 5/6 p. 332-355.
Ferruti P et al., "Synthesis, characterisation and antitumour activity of platinum (II) complexes of novel functionalised Poly (amido amines)s" Macromolecular Chemistry and Physics, Wiley-Vch Verlag, Weinheim, DE, vol. 200, No. 7, 1999 pp. 1644-1654.
Holzapfel et al., "Synthesis and biomedical applications of functionalized fluorescent and magnetic dual reporter nanoparticles as obtained in the miniemulsion process" Journal of Physics: Condensed Matter, Institute of Physics Publishing , vol. 18, 2006, pp. S2581-S2594.
Morais et al., "Preparation and characterization of ultra-stable biocompatible magnetic fluids using citrate-coated cobalt ferrite nanoparticles" Thin Solid Films, Elsevier, vol. 515, 2006, pp. 266-270.

* cited by examiner

*Primary Examiner* — Michael G Hartley
*Assistant Examiner* — Jagadishwar Samala
(74) *Attorney, Agent, or Firm* — Snell & Wilmer LLP

(57) ABSTRACT

There are described nanoparticles of magnetic metal oxides employable in constructs consisting in polymer particles possibly also incorporating pharmacologically active substances.

19 Claims, 1 Drawing Sheet

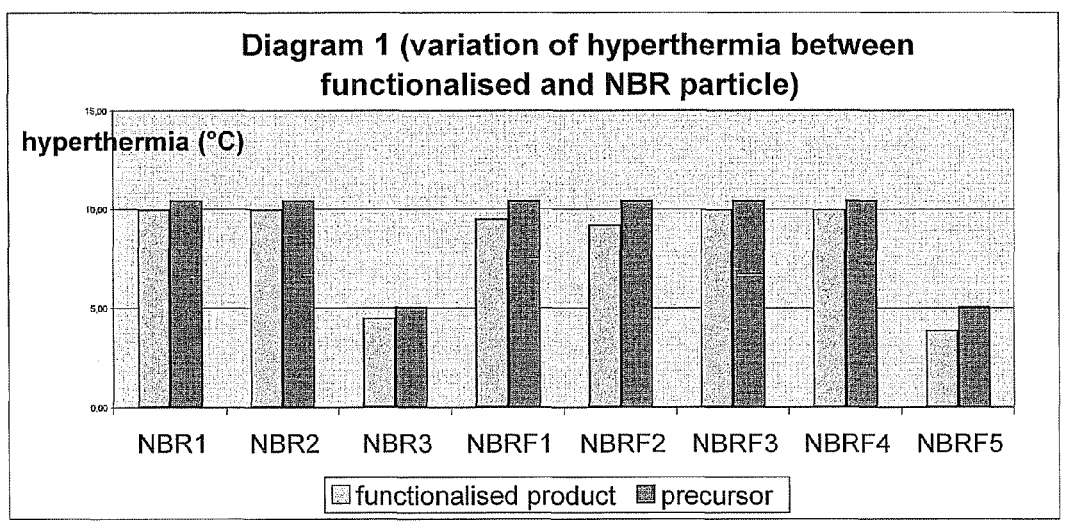

MAGNETIC NANOPARTICLES FOR THE APPLICATION IN HYPERTHERMIA, PREPARATION THEREOF AND USE IN CONSTRUCTS HAVING A PHARMACOLOGICAL APPLICATION

FIELD OF THE INVENTION

The present invention relates to the field of nanometric particles, specifically metal oxides having magnetic properties, and to the use thereof in the pharmacological field.

STATE OF THE ART

Nanoparticles are objects having a diameter below 300 nm. In recent years, there has been a great interest in the scientific and technological community for the peculiar chemical-physical properties of these materials.

Specifically, magnetic nanoparticles have their potential field of application in the diagnostic sector as a contrast medium in imaging techniques (magnetic resonance), in the magnetic localisation techniques and, mainly, in the specifically therapeutic field of hyperthermia mediated by magnetic fields.

The main feature of these materials essentially consists in four elements:
- the composition of the central core of the particles (which must comprise materials having magnetic characteristics);
- the size of the magnetic central core (which results being of the order of tens of nanometers or less)
- the stability in a physiological environment
- the biocompatibility.

The actual usefulness of the magnetic nanoparticles is, in the ultimate analysis, related to their ability to increase the temperature of the medium in which they are confined when interacting with an external electromagnetic fields.

Many patents discuss magnetic nanoparticles coated with biocompatible materials so as to obtain composite particles having a diameter in the range between 5 and 500 nm, which may form stable suspensions in an aqueous system. See U.S. Pat. No. 5,427,767, Kresse; U.S. Pat. No. 6,255,477, Kleiber et al.; U.S. Pat. No. 6,541,039, Lesniak.

A particular attention has been directed to methods to obtain metal oxides forming the core of the particles, and all of these are focused on obtaining iron oxides. See U.S. Pat. No. 4,677,027, Porath; U.S. Pat. No. 5,160,725, Pilgrim; U.S. Pat. No. 4,329,241, Massart; U.S. Pat. No. 4,101,435, Hasegswa.

In all of the cited patents, even though in some cases they are generally referred to as "metal oxides" or "iron oxides doped with other metal elements", the examples set forth only specifically refer to the iron oxides in their various forms and no cases of hyperthermic effect related to other kinds of metal oxides are cited.

In general, these nanoparticulate oxides have a low hyperthermic efficiency and it is therefore required to introduce high amounts thereof in order to obtain a therapeutic result.

Furthermore, there is a broad series of patents relating to the methods to obtain various kinds of coatings, stabilisers and protections for the magnetic particles by means of different methods. See U.S. Pat. No. 4,280,918, Homola; U.S. Pat. No. 6,576,221, Kresse; U.S. Pat. No. 4,452,773, Molday; U.S. Pat. No. 4,827,945, Groman; U.S. Pat. No. 5,545,395, Tournier; EP 0272091, Eley.

A series of different techniques for the production of polymer nanoparticles internally incorporating pharmacologically active products is described; these techniques may be grouped in four classes:

a) trapping techniques of the drug in polymers insoluble in water and soluble in solvents miscible with water.
b) Coacervation techniques of the (water-soluble) drug with proteins or polymers soluble in water, followed by the formation of nanoparticles by dilution with solvents in which the proteins or the polymers are insoluble, the stabilisation of the nanoparticulate structure with appropriate bonding agents and the removal of the "precipitating" agent.
c) Incorporating techniques of the (water-soluble or water-insoluble) drug by emulsification in the presence of surface agents, which leads to the formation of micrometric particles, followed by the removal of the solvent to reduce the size of the particles to nanometric levels.
d) Incorporating techniques of the (water-soluble or water-insoluble) drug by emulsification in the presence of proteins, which leads to the formation of micrometric particles, followed by the removal of the solvent to reduce the size of the particles to nanometric levels.

It may be noted that the description of such a high number of methods, each having its specific variants, is already an indication of the difficulties encountered to obtain the desired product having a size suitable for use (generally in the range between 100 and 300 nm), a restricted size distribution and the ability to remain stable in a physiological environment.

Taking into account the considered techniques, the following problems may be noted:
- the trapping techniques for the "active substance" in polymers insoluble in water and soluble in appropriate organic solvents leads to a "simple" formation of nanoparticles, the size of which are mainly determined by the concentration of the polymer and drug and by the solvent/water dilution ratio. The main problem consists in that the nanometric particles obtained in this manner are stable in water but already unstable in a physiological solution and the use thereof in the biomedical field is therefore hardly acceptable.
- The coacervation techniques of the (water-soluble) drug with proteins soluble in water, followed by the formation of nanoparticles by dilution with solvents, the stabilisation of the nanoparticulate structure with appropriate bonding agents and the removal of the "precipitating" solvent are definitely not employable for products insoluble in water. On the other hand, the advantage of using nanoparticulate systems is reduced for products which are already soluble in an aqueous environment, because these active substances may also be directly administered with similar effects to those obtained with the nanoparticulate system.
- The emulsification techniques in the presence of surface agents always display the problem of the emulsifying system hardly being able to combine the ability to form small enough micelles having the compatibility with the human organism at the concentrations employed.
- The incorporating techniques of the (water-soluble or water-insoluble) drug by emulsification in the presence of proteins display great technical difficulties as far as the productive-type applications are concerned. The emulsification in these cases is very difficult and forces to use complex techniques, having low industrial productivity, which are very expensive (for instance, high pressure emulsification techniques).

In light of what has been set forth above, it is evident the need to have nanoparticulate magnetic oxides having a high hyperthermic efficiency and incorporation methods for magnetic systems and pharmacological principles, leading to the preparation of constructs that are effective from a hyperthermic and pharmacological point of view while also being stable and biologically compatible.

BRIEF DESCRIPTION OF THE DRAWINGS

FIG. 1 is a diagram wherein the hyperthermic efficiency of a functionalised particle and the corresponding final construct are compared, said efficiency being expressed as a $\Delta T$ in ° C.

SUMMARY OF THE INVENTION

The present invention relates to magnetic metal oxide nanometric particles and to constructs consisting of: said magnetic nanometric particle, possibly functionalised with bifunctional compounds, a polymer possibly containing a pharmacologically active molecule and, when said polymer is insoluble in water, an external protecting layer of surface agents, and to the use thereof in hyperthermic treatments.

DETAILED DESCRIPTION OF THE INVENTION

The present invention allows to overcome the aforementioned problems thanks to constructs comprising: a magnetic nanometric particle, possibly functionalised with bifunctional compounds, a polymer possibly containing a pharmacologically active molecule and, when said polymer is insoluble in water, an external protecting layer of surface agents.

The above said pharmacological active molecule, when present can be connected to the polymer or dispersed in it.

The nanometric particles according to the invention are spinels and oxides of the $M^{II}M^{III}_2O_4$ type, in which $M^{II}$=Fe, Co, Ni, Zn, Mn; $M^{III}$=Fe, Cr) in a nanometric form.

Among the aforementioned spinels, it has been unexpectedly found that cobalt ferrite has a high hyperthermic efficiency.

Among other spinels and iron oxides, it has also unexpectedly been discovered that controlled size magnetite and maghemite, which are prepared according to the methods described in the present invention, have a better hyperthermic efficiency than similar products described in the literature.

The bifunctional compounds according to the invention are intended: thiols, carboxylic acids, hydroxamic acids, phosphoric acids, esters and salts thereof having an aliphatic chain that carries a second functional group at the terminal position (designated ω).

More specifically, the bifunctional compounds are compounds of the general formula:

In which:
n is an integer in the range between 2 and 20;
$R_1$ is chosen from: CONHOH, CONHOR, PO(OH)$_2$, PO(OH)(OR), COOH, COOR, SH, SR;
$R_2$ is the external group and is chosen from: OH, NH$_2$, COOH, COOR;
R is an alkyl group or an alkaline metal.

Among alkaline metal preferred are K, Na, or Li, while among the alkyl group preferred are $C_{1-6}$alkyl, more particularly ethyl.

Particularly preferred among the above said difunctional groups is the ethyl-12-(hydroxyamino)-12-oxododecanoate.

The polymers constituting the construct can be water-soluble polymers or water insoluble polymers stabilised by surface agents.

The water-soluble polymers according to the invention are, for example, polyelectrolytes, polypeptides and water-soluble proteins; water-soluble polymers chosen from block copolymers, modified polyethylene glycols, modified polysaccharides, phospholipids, polyamineamides, globular proteins are preferred. The water insoluble polymers are, for example, chosen among: polyesters, polyamides, polyanhydrides, polyorthoesters, peptides, polyamineamides; or insoluble organic molecules like for example cholesterole; polyesters and cholesterole are preferred.

Surface agents according to the invention may be: polyelectrolytes, polypeptides and water-soluble proteins; block copolymers, modified polyethylene glycols, modified polysaccharides, phospholipids, polyamineamides, globular proteins; preferred are human serum proteins and pluronics block copolymers.

The polymers are known or can be easily obtained according to methods known in the art as by polyaddition of primary monoamines or secondary diamines with bis.acrylamides, at room temperature for a time comprised between some hours and some days as for example reported in *Macromolecular Rapid Communication*, 2002, 23, No. 5/6 p. 332-355.

Example of polymers, both water soluble and surface agents, according to the invention are:

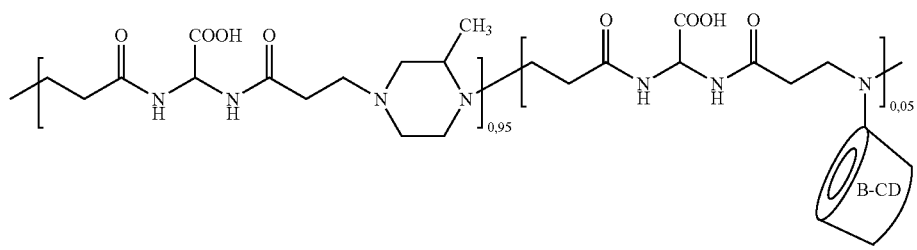

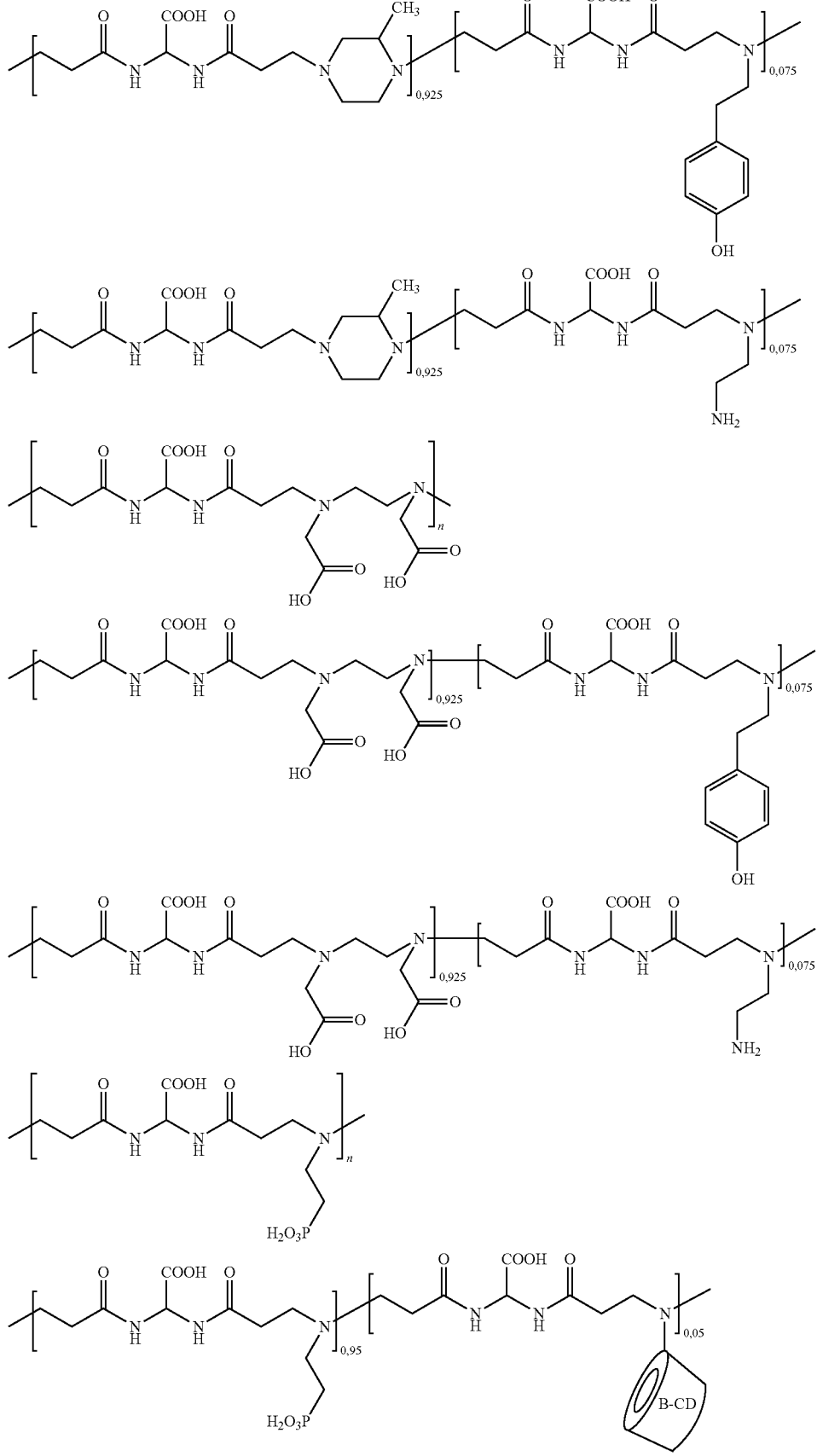

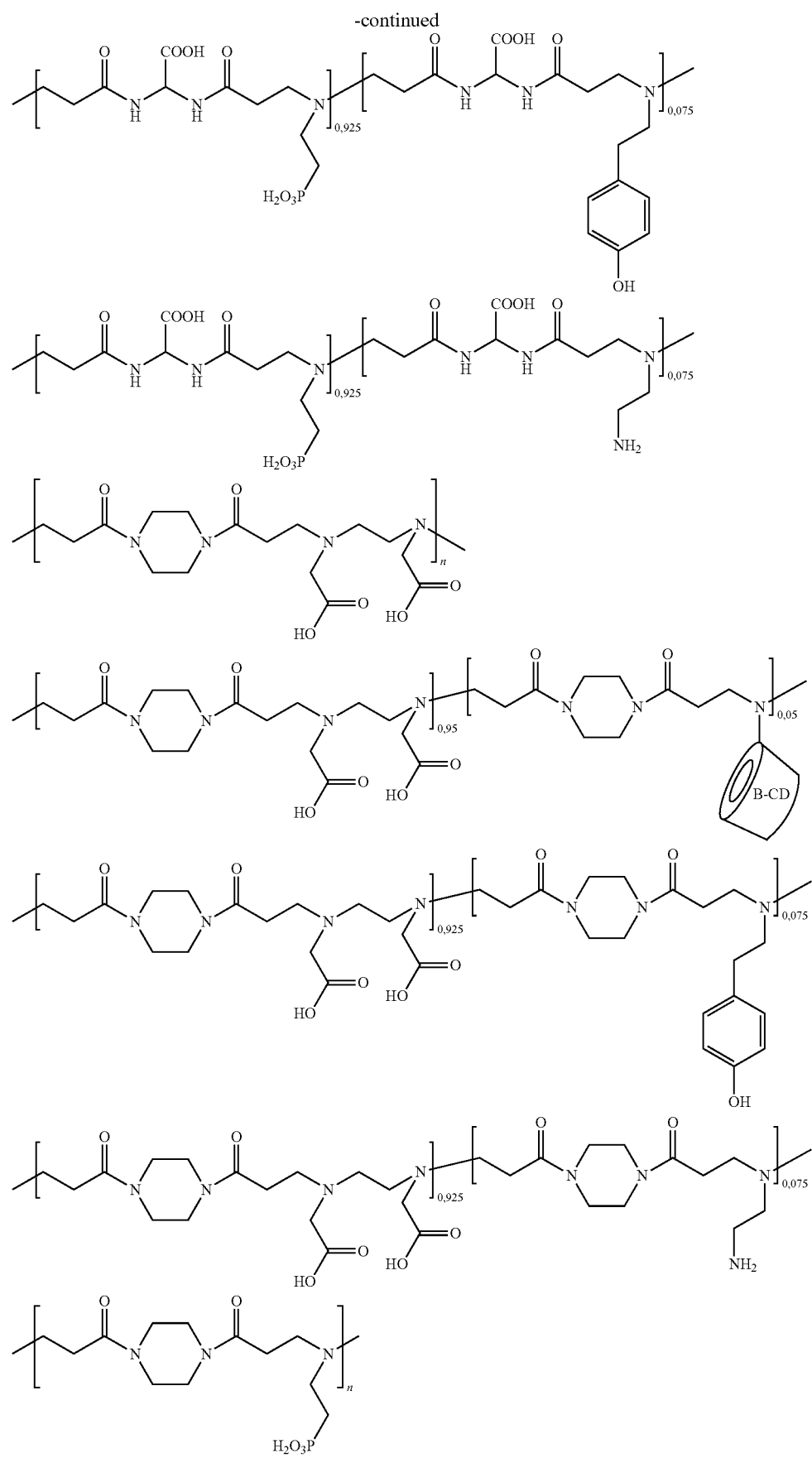

-continued
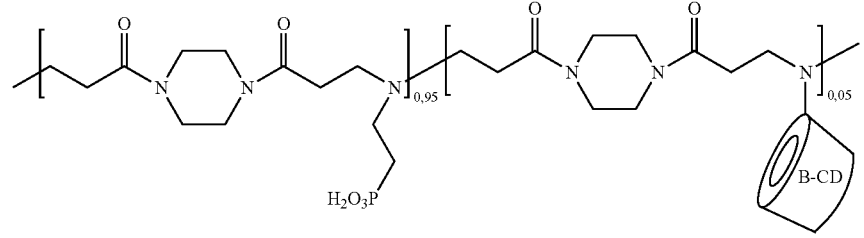
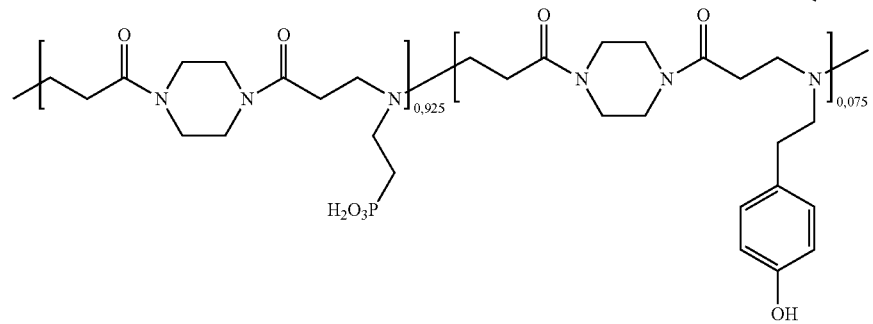
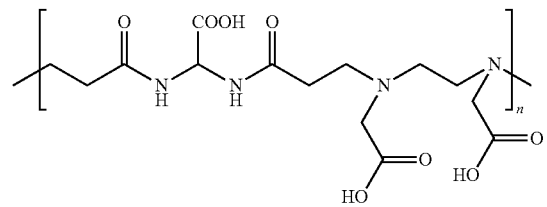
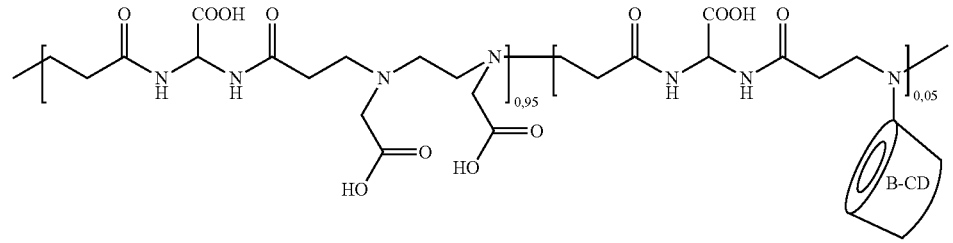
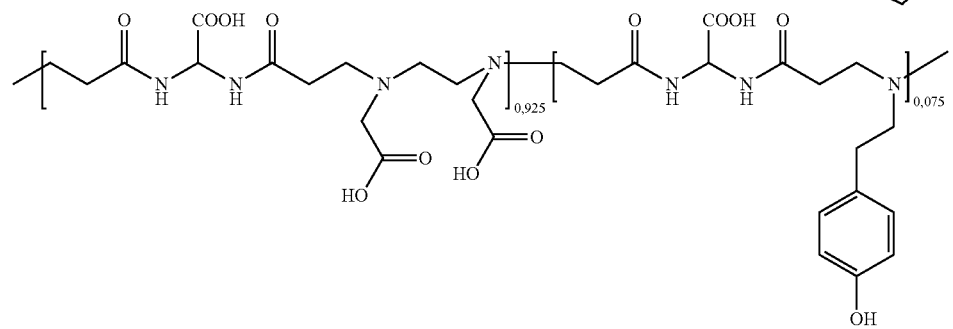
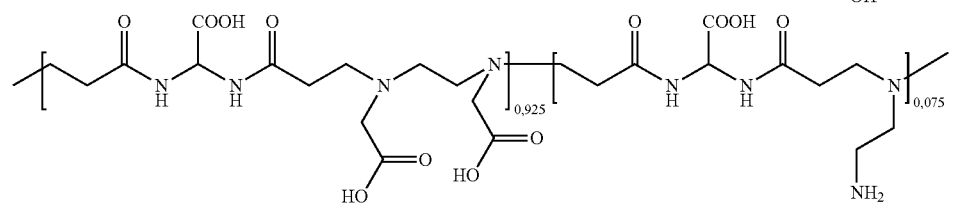
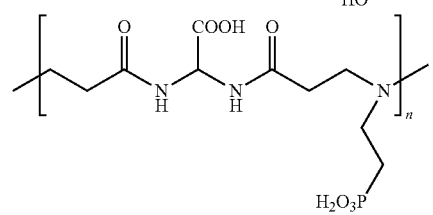

-continued
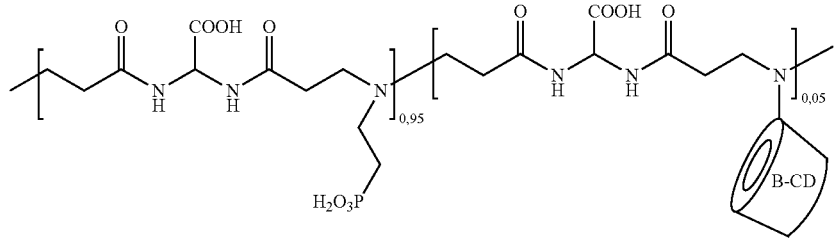
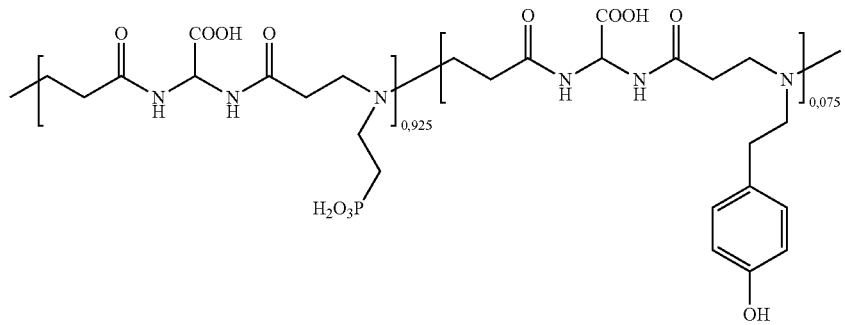
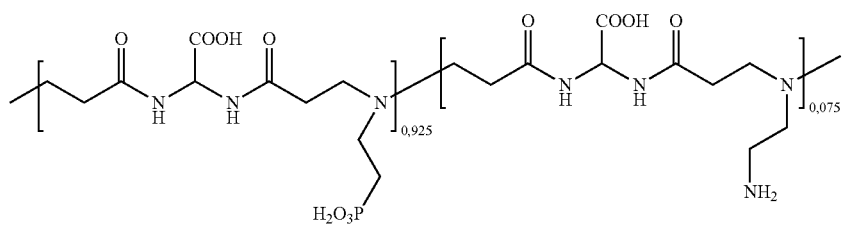
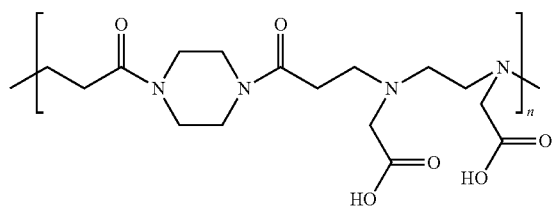
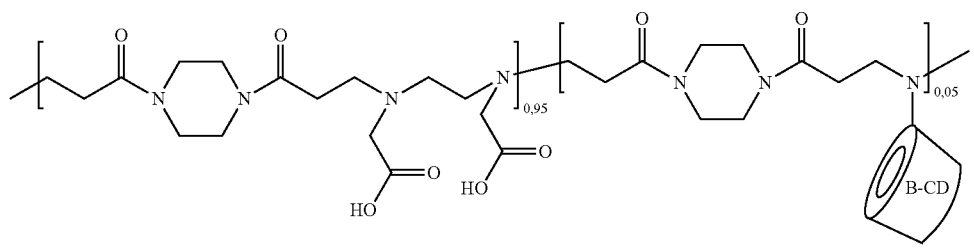
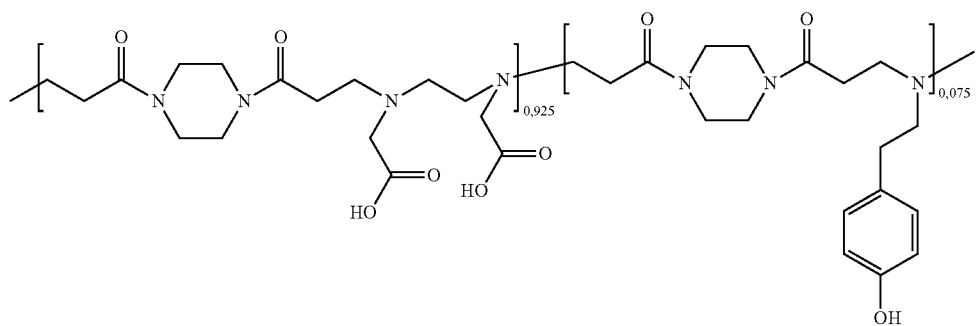

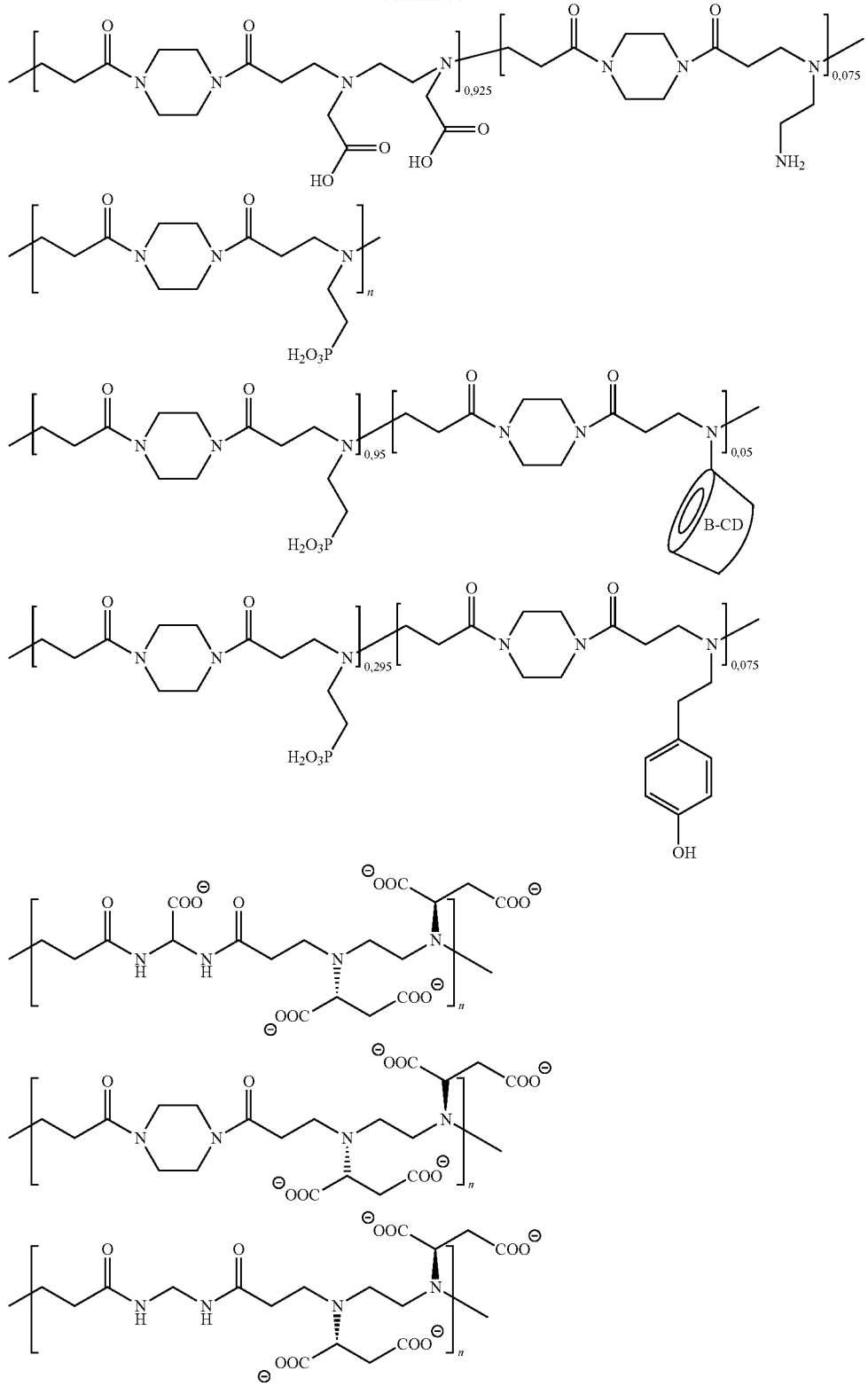

wherein n is comprised between 3-300, preferably between 10-100.

Pharmacologically active molecules according to the invention are the biologically active molecules normally used in the various therapies, for example antitumour agents (such as anthracycline), antimicrobial agents, anti-inflammatory agents, immunomodulators, molecules acting on the central nervous system etc. or those capable of marking the cells so as to allow their identification with the normal means of diagnostic detection (for example fluorescent stains).

The methods for the preparation of the constructs described in the present invention are extremely flexible.

Furthermore, thanks to the possibility of controlling their size and therefore their hyperthermic properties, the magnetic nanoparticles according to the present invention are especially suitable for the preparation of biocompatible nanoparticulate constructs which are extremely flexible and active even at low concentrations of magnetic nanoparticles.

This is certainly an advantage in all potential biomedical applications. In the case in which the constructs are based on hydrophilic polymers used as surfactant agents, it is known that it is required to use amounts of surfactant greater than 300% with respect to the pharmacologically active product; by the use of the nanoparticles according to the present invention the amount of surfactant, which notoriously has a poor biocompatibility, may considerably be decreased.

Specifically regarding cobalt ferrite, it has been unexpectedly found that, the size being equivalent, it has a hyperthermic efficiency of approximately one order of magnitude more than that of iron oxides; furthermore, in contrast to that occurring with iron oxides described in the literature, the hyperthermic properties of the physically immobilised nanoparticles of cobalt ferrite do not vary with respect to the material dispersed in a fluid matrix. This makes them more efficient in those cases in which the extracellular matrix or the cytosolic matrix represents an obstacle for their rotation.

When irradiated with electromagnetic waves having a frequency in the range between 10 and 1000 kHz, preferably between 50 and 500 kHz, the cobalt ferrite nanoparticles have a far better hyperthermic behaviour with respect to the iron oxides having equivalent nanoparticle size (also doped with impurities of Co, Ni or other metal elements). At the aforementioned frequencies, the magnetite and maghemite particles we prepared also displayed better hyperthermic efficiencies than the equivalents described in literature.

The magnetic nanoparticles according to the invention may be prepared according to known processes as e.g. the polyol process widely described in the literature which, briefly, consists in the use of a high boiling alcohol allowing to operate at high temperatures and lead the forming particles to give rise to complexes thus preventing the growth thereof.

Normally, the desired metal precursors (preferably acetates, carbonates, sulphates, oxalates, chlorides) are added to a known volume of alcohol (e.g. diethylene glycol, DEG). The solution is then heated while mixing to the complete solubilisation of the precursors, water is possibly added in an appropriate amount to facilitate the hydrolysis of the precursors, it is heated for a few hours at a temperature higher than 150° C. and it is then left to cool, thus obtaining a stable suspension of monodispersed nanoparticles with a restricted size distribution.

Moreover since the hyperthermic effect of the cobalt ferrite is far more dependent on the size of the nanoparticles than that occurring for magnetite or maghemite new synthesis methods, allowing to control the size of the nanoparticles in a reproducible manner and, accordingly, the hyperthermic effect thereof, have been designed and are also part of the present invention. The size control has also brought great advantages in the synthesis of magnetite and maghemite allowing to obtain products alternative to cobalt ferrite and more efficient than their equivalents from the hyperthermic point of view.

New synthesis methods, which are capable of allowing the size control (and therefore hyperthermia) of the magnetic nanoparticles which are always obtained in a suspension are reported hereinafter.

Continuous Process.

In this case the procedure is carried out as described above for the polyol process, but the synthesis is performed with the addition (in an amount equimolar to the reagents) of a "primer" consisting of previously synthesised nanoparticles. In this way, at the end of the reaction magnetic nanoparticles having greater size than those introduced at the beginning of the synthesis are obtained.

In practice, the procedure for a first preparation is performed as for the polyol process; subsequently, a new reaction is carried out in the same conditions as the first, with all of the starting materials in amounts identical to those already used and with the addition of the product obtained from the first reaction. The magnetic nanoparticles thus obtained (which are twofold and have greater size with respect to those introduced at the beginning of the synthesis) may be used again as a "primer" for the following reaction. The cycle may be repeated an indefinite number of times until the particles displaying the desired size are obtained.

Semicontinuous Substitution Process.

In practice, a first synthesis according to the polyol process is performed, but at the end of the stationary heating period at 180° C. the product is not cooled, but rather poured in a flask having twice the size, in which all of the starting materials have been loaded in amounts identical to the product which has already been reacted. The temperature is taken to 180° C. again, it is maintained for 3 hours and the cycle is then repeated for a variable number of times until the product having the desired size is obtained.

Growth Process.

In this case, the synthesis is performed according to the above described polyol process, but the period during which the product is maintained at a temperature of 180° C. is prolonged for a variable number of hours. Therefore, a product is obtained, the dimensions of which are dependent on time of temperature persistence.

Moreover, the magnetic nanoparticles may further be prepared by a process similar to the above described polyol process, though performing the heating exclusively in a microwave oven which allows to considerably reduce the reaction times and to have a better control on the size and morphology.

As a further advantage of the above described processes it must be considered that by means of these preparative techniques, the stechiometry of the nanoparticles may be modified: e.g. maghemite may be produced from the magnetite obtained, according to one of the previous processes, by the oxidation thereof at a controlled temperature in an acetic oxidising environment thus accelerating the oxidative process which would naturally occur although by much longer times. In this case, the size control of the magnetic nanoparticles is performed in an indirect manner carrying out a size control of the magnetite precursor according to one of the previously described methods.

The nanoparticulate cobalt ferrite, magnetite and maghemite obtained according to the described method have been controlled for the size of the particles by means of DLS (Malvern Zetasizer nano-S).

The nanoparticles thus obtained have a size in the range between 4 and 200 nm, preferably between 10 and 70 nm.

The functionalisation of the nanoparticles was obtained according to known methods or as described in patent PCT/EP2007/050036, i.e. by reacting bifunctional derivatives dissolved in ethanol with the nanoparticles as defined above so as to coat the surface thereof.

The process for the preparation occurs by reacting a nanoparticle dispersion in an organic solvent (e.g. ethylene glycol) with the chosen bonding agent while mixing at reduced temperature for a few hours. The product is then possibly separated by extraction with particular solvents or precipitated, e.g. with acetone, spun in a centrifuge, separated and possibly redispersed in a suitable solvent.

The aforementioned polymeric constructs have different characteristics depending on the type of polymer employed for the preparation thereof.

Specifically, the polymers may be insoluble or soluble in water; and their use in the synthesis of the constructs according to the invention are reported hereinafter.

Constructs Based on Water-Insoluble Polymers

They consist in magnetic nanoparticles, functionalised as above said, in combination with a pharmacologically active agent, incorporated in a water-insoluble polymer, as previously defined, in turn stabilised by surface agents as above defined.

Surface agents according to the invention may be: polyelectrolytes, polypeptides and water-soluble proteins; surface agents chosen from block copolymers, modified polyethylene glycols, modified polysaccharides, phospholipids, polyamineamides, globular proteins are preferred. The process for the preparation of these constructs according to the invention is a continuous and single step process for the incorporation of magnetic nanoparticles in a water-insoluble polymer matrix and for the coating of this structure with suitable surface agents.

The procedure implies the use of water (in which the surface agent is previously dissolved) and an organic solvent miscible therewith (to a greater extent than 10%), in which the magnetic nanoparticles, functionalised as above described, and the polymer matrix are previously solubilised. The two liquids are then mixed in appropriate conditions so as to obtain a self-assembly of the components previously solubilised in the phases to form a controlled size construct.

The incorporation of the drug in the construct occurs in the assembly step by solubilisation in water or organic solvent. In this way, the number of pharmacologically active species which may be introduced in the construct increases.

This method allows to obtain the final product with yields in the range between 90 and 99%, unexpectedly the hyperthermic efficiency of the construct thus assembled is similar to that of the starting inorganic particles.

The average diameter of the construct is in the range between 50 and 300 nm and the ratio between the concentration of the possibly present drug and the concentration of the magnetic particles may easily be varied during assembly.

The close association of magnetic particles and drug allows to obtain the controlled release of the drug by thermal effect induced by the interaction of the magnetic nanoparticles with an external electromagnetic field.

In this manner, magnetic hyperthermia may be obtained on one side and a synergic effect with the pharmacologically active species may be obtained on the other side.

The presence of magnetic particles in a percentage variable with respect to the drug allows to enhance the hyperthermic effect i.e. the strictly pharmacological effect in the most indicated manner for the specific pathology to be treated.

The constructs obtained are stable in a physiological solution environment and thus prove to be suitable for a therapeutic use.

Constructs Based on Water-Soluble Polymers:

They consist in magnetic nanoparticles, functionalised as above said, possibly in combination with a pharmacologically active agent, incorporated in a water-soluble polymer or in surface agents as above defined.

The process according to the invention implies an organic solvent miscible in water to an extent greater than 10% as a "carrier" solvent for the magnetic particles and the drug.

The procedure implies the use of water (in which the water-soluble polymer is previously dissolved) and a liquid miscible with water (to an extent greater than 10%) in which the functionalised magnetic nanoparticles are previously solubilised. The two liquids are then mixed in appropriate conditions so as to obtain a self-assembly of the components previously solubilised in the steps to form a controlled size construct.

The incorporation of the drug in the construct occurs in the assembly step by solubilisation in water or in an organic solvent. In this manner, the number of pharmacologically active species which may be introduced in the construct increases and the ratio between the concentration of the drug and the concentration of the magnetic particles may be easily varied.

In this manner, constructs having an average diameter between 30 and 100 nm and a very restricted size distribution (polydispersion index PDI=0.10-0.15) may be obtained, whereas by the methods described in the literature (with a more complex and hardly scalable method) particles having a size of about 200 nm with a broader polydispersion index (about 0.25) are obtained. This method allows to obtain the final product with yields in the range between 80 and 98%, unexpectedly the hyperthermic efficiency of the construct thus assembled is similar to that of the starting inorganic particles.

The resulting constructs are stable in a physiological solution environment and thus prove suitable for a therapeutic use.

The possibility to obtain such small constructs, evenly distributed and stable in a physiological environment represents a great advantage for possible therapeutic application because the particles may diffuse better in the body areas to be treated, are more difficult for the immune system to detect and thus eliminate and are more easily incorporated within target cells (I. Brigger, C. Dubernet, P. Couvreur, Adv. Del Rev., 2002, 54, 631. Nanoparticles in cancer therapy and diagnosis).

The overall data for the synthesised nanoparticles, the functionalised nanoparticles, and the constructs as defined above are set forth in Table 1, which is subdivided as follows:
Tables 1(a) and 1(b): magnetic particles;
Table 1(c): functionalised magnetic particles;
Table 1(d): constructs with polymer coating.

In Table 2, the size of the resulting particles are set forth with the processes according to the invention, while the corresponding hyperthermic effect is set forth in Table 3.

The overall data of the functionalised nanoparticles are set forth in Table 4 in which the starting products, the type of functionalisation and the hyperthermic effect (expressed as a $\Delta T$) of the precursor and the final product in the same measurement conditions are indicated.

From Diagram 1, it is apparent that the hyperthermic effect of the construct is always similar to that of the precursor.

The crystal structure of the samples has been identified by means of X-ray diffraction (XRD) recording the reflections in the range of 10-700 with a scanning range of $0.05°(2\Theta)$ for 5 s on a Philips X'pert Pro diffractometer (Cu K$\alpha$ radiation).

The size of the crystallites has been determined by diffraction peaks by using the Scherrer method.

The samples thus characterised (non functionalised particles, functionalised particles, final constructs) have been subjected to hyperthermia tests, for which the samples have been dispersed in various mediums and an oscillating magnetic field radiating unit Novastar 5 W to 5 Kw provided by Ameritherm has been used. The tests have been carried out in adiabatic conditions with an electromagnetic field of 170 kHz and having a magnetic field intensity of 21 kA/m$^2$, using an alumina crucible having a capacity of 0.30 ml completely filled with a dispersion of the sample in a suitable solvent. The concentration of the sample (expressed as concentration in metal oxide) in the dispersing medium is in the range between 0.1% and 3%.

The initial and final temperature of the dispersion has been measured by a FLIR E65 thermocamera.

For better illustrating the invention the following Examples are reported.

Example 1

Preparation of Nanometric Cobalt Ferrite According to the Known Process (Polyol Process)

Product formula: NFeCo31
Reagents Used:
Fe:Co ratio=2:1
9.53 g Co(Ac)$_2$.4H$_2$O (23.7% Co w/w)
Co(II)=2.259 g=0.038 moles
21.42 g Fe(CH$_3$COO)$_3$ (Sheperd pasta; c. 20% Fe w/w)
Fe(III)=4.284 g=0.077 moles
269.04 g DEG
Synthesis:

A 4-necked flask is equipped with a blade stirrer, a bubble condenser provided with a valve for a possible distillation, a probe and a stopper (addition neck). The reagents are placed with the DEG in the reaction flask. The system is taken to the temperature of 110° C. for the solubilisation step (time: 1 h). Subsequently, the temperature is raised to 180° C. and the system is left at reflux for 3 hours. The process performed while mixing leads to the formation of a black suspension.

Example 2

Preparation of Nanometric Magnetite According to the Known Process (Polyol Process)

Product formula: Fe74
Reagents:
Fe III:Fe II ratio=2:1
30.32 g Fe(Ac)$_2$ solution (7% Fe w/w)
Fe(II)=2.122 g=0.038 moles
21.42 g Fe(CH$_3$COO)$_3$ (Sheperd pasta; c. 20% Fe w/w)
Fe(III)=4.284 g=0.077 moles 269.04 g DEG
Synthesis:

A 4-necked flask is equipped with a blade stirrer, a bubble condenser provided with a reflux and distillation two-way system, a probe and a stopper (addition neck). The reagents are placed with the DEG in the reaction flask. The system is taken to the temperature of 120° C. for the stabilisation step and maintained for one hour at such a temperature. Subsequently, the mixture is heated to 180° C. maintaining the distillation step. Having reached the internal temperature of 180° C., the system is left at reflux for 3 hours. The process performed while mixing leads to the formation of a brown suspension.

Example 3

Preparation of a Nanometric Mixed Fe$^{III}$, Fe$^{II}$, Ni Spinel According to the Known Process (Polyol Process)

Product formula: Fe Do Ni 03
Reagents Specifications:

| | |
|---|---|
| Fe(CH$_3$COO)$_3$ | MW = 232.98 g/moles |
| Fe(CH$_3$COO)$_2$ | MW = 173.93 g/moles |
| Ni(CH$_3$COO)$_2$ | MW = 176.78 g/moles |
| Fe | MW = 55.85 g/moles |
| Ni | MW = 58.69 g/moles |
| DEG | MW = 106.12 g/moles |

Reagents:
Fe$^{III}$:Fe$^{II}$:Ni ratio=8:3:1
22.34 g Fe(Ac)$_3$ (Sheperd pasta; c. 20% Fe w/w)
Fe(III)=4.468 g=80 mmoles
23.94 g Fe(Ac)$_2$ solution (7% w/w in Co)
Fe(II)=1.675 g=30 mmoles
1.77 g Ni(Ac)$_2$
Ni=0.588 g=10 mmoles
269.04 g DEG
Synthesis:

A 4-necked flask is equipped with a blade stirrer, a bubble condenser provided with a reflux and distillation two-way system, a probe and a stopper (addition neck). The reagents are placed with the DEG in the reaction flask. The system is taken to the temperature of 110° C. for the stabilisation step and maintained for 1 hour at such a temperature. Subsequently, the mixture is heated to 180° C. maintaining the distillation step. Having reached the internal temperature of 180° C., the system is left at reflux for 3 hours. The process performed while mixing leads to the formation of a brown suspension.

Example 4

Preparation of Nanometric Cobalt Ferrite by the Continuous Process According to the Present Invention Product formula: NFeCo36 Stage 1 (Product formula: NFeCo35)
Reagents Specifications:

| | |
|---|---|
| Fe(CH$_3$COO)$_3$ | MW = 232.98 g/moles |
| Co(CH$_3$COO)$_2$•4H$_2$O | MW = 248.93 g/moles |
| CoFe$_2$O$_4$(NFeCo31) | MW = 234.62 g/moles |
| Co | MW = 58.93 g/moles |
| Fe | MW = 55.85 g/moles |
| DEG | MW = 106.12 g/moles |

Reagents:
Fe:Co ratio=2:1
9.53 g Co(Ac)$_2$.4H$_2$O (23.7% Co w/w)
Co(II)=2.259 g=0.038 moles
21.42 g Fe(CH$_3$COO)$_3$ (Sheperd pasta; c. 20% Fe w/w)
Fe(III)=4.284 g=0.077 moles
269.04 g DEG
287 g NFeCo 31

Synthesis:

A 4-necked flask is equipped with a blade stirrer, a bubble condenser provided with a valve for the possible distillation, a probe and a stopper (addition neck). The reagents are placed with the DEG in the reaction flask. The system is taken to the temperature of 110° C. for the solubilisation step (time: 1 h). Subsequently, the temperature is raised to 180° C. and the system is left at reflux for 3 hours. The process performed while mixing leads to the formation of a black suspension. 570 g of the product are obtained.

Step 2 (Product Formula: NFeCo36)
Reagents specifications: as above
Reagents:
Fe:Co ratio=2:1
19.06 g $Co(Ac)_{2\text{-}4}H_2O$ (23.7% Co w/w)
Co(II)=4.518 g=0.076 moles
42.84 g $Fe(CH_3COO)_3$ (Sheperd pasta; c. 20% Fe w/w)
Fe(III)=8.568 g=0.154 moles
538 g DEG
570 g NFeCO_35
Synthesis:

A 4-necked flask is equipped with a blade stirrer, a bubble condenser provided with a valve for the possible distillation, a probe and a stopper (addition neck). The reagents are placed with the DEG in the reaction flask. The system is taken to the temperature of 110° C. for the solubilisation step (time: 1 h). Subsequently, the temperature is raised to 180° C. and the system is left at reflux for 3 hours. The process performed while mixing leads to the formation of a black suspension. 1105 g of the product are obtained.

Example 5

Preparation of Nanometric Magnetite Product Formula Fe76 with the Continuous Process According to the Present Invention Stage 1 (Product Formula Fe75)
Reagents Specifications:

| | |
|---|---|
| $Fe(CH_3COO)_3$ | MW = 232.98 g/moles |
| $Fe(CH_3COO)_2$ | MW = 248.93 g/moles |
| $Fe_3O_4(Fe74)$ | MW = 231.53 g/moles |
| Fe | MW = 55.85 g/moles |
| DEG | MW = 106.12 g/moles |

Reagents:
$Fe^{III}:Fe^{II}$ ratio=2:1
30.32 g $Fe(Ac)_2$ solution (7% Fe w/w)
Fe(II)=2.122 g=0.038 moles
21.42 g $Fe(CH_3COO)_3$ (Sheperd pasta; c. 20% Fe w/w)
Fe(III)=4.284 g=0.077 moles
269.04 g DEG
279 g Fe74
Synthesis:

A 4-necked flask is equipped with a blade stirrer, a bubble condenser provided with a reflux and distillation two-way system, a probe and a stopper (addition neck). The reagents are placed with the DEG in the reaction flask. The system is taken to the temperature of 120° C. for the stabilisation step and maintained for 1 hour at such a temperature. Subsequently, the mixture is heated to 180° C. maintaining the distillation step. Having reached the internal temperature of 180° C., the system is left at reflux for 3 hours. The process performed while mixing leads to the formation of a brown suspension.

Total obtained: 552 g.
Stage 2 (Product formula: Fe76)
Reagents specifications: as above
Reagents:
Fe III:Fe II ratio=2:1
60.64 g $Fe(Ac)_2$ solution (7% Fe w/w)
Fe(II)=4.244 g=0.076 moles
42.84 g $Fe(CH_3COO)_3$ (Sheperd pasta; c. 20% Fe w/w)
Fe(III)=8.568 g=0.154 moles
538.08 g DEG
552 g Fe75
Synthesis:

A 4-necked flask is equipped with a blade stirrer, a bubble condenser provided with a reflux and distillation two-way system, a probe and a stopper (addition neck). The reagents are placed with the DEG in the reaction flask. The system is taken to the temperature of 120° C. for the stabilisation step and maintained for 1 hour at such a temperature. Subsequently, the mixture is heated to 180° C. maintaining the distillation step. Having reached the internal temperature of 180° C., the system is left at reflux for 3 hours. The process performed while mixing leads to the formation of a brown suspension.

Total obtained: 1113 g.

Example 6

Process for the preparation of cobalt ferrite with the method of the semicontinuous substitutions according to the present invention. Product formula: NFeCoCONT-03B3
Stage 1 (Product Formula: NFeCoCONT-03B1)
Reagents Specifications:

| | |
|---|---|
| $Fe(CH_3COO)3$ | MW = 232.98 g/moles |
| $Co(CH_3COO)_2 \cdot 4H_2O$ | MW = 248.93 g/moles |
| $CoFe_2O_4(NFeCo31)$ | MW = 234.62 g/moles |
| Co | MW = 58.93 g/moles |
| Fe | MW = 55.85 g/moles |
| DEG | MW = 106.12 g/moles |

Reagents:
Fe:Co ratio=2:1
9.53 g $Co(Ac)_{2\text{-}4}H_2O$ (23.7% Co w/w)
Co(II)=2.259 g=0.038 moles
21.42 g $Fe(CH_3COO)_3$ (Sheperd pasta; c. 20% Fe w/w)
Fe(III)=4.284 g=0.077 moles
269.04 g DEG
285 g NFeCO_31
Synthesis:

A 1 liter 4-necked flask is equipped with a blade stirrer, a bubble condenser provided with a valve for the possible distillation, a probe and a stopper (addition neck). The cobalt acetate and the iron acetate are placed with the DEG in the reaction flask and NFeCo31 which is still warm from the previous reaction is added. The temperature is taken to 180° C. and the system is left at reflux for 3 hours. 575 g of the product are obtained.
Stage 2 (Product Formula: NFeCoCONT-03B2)
Reagents specifications: as above
Reagents:
Fe:Co ratio=2:1
19.06 g $Co(Ac)_{2\text{-}4}H_2O$ (23.7% Co w/w)
Co(II)=4.518 g=0.076 moles
42.84 g $Fe(CH_3COO)_3$ (Sheperd pasta; c. 20% Fe w/w)
Fe(III)=8.568 g=0.154 moles
538 g DEG
575 g NFeCoCONT-03B1

Synthesis:

A 2 liter 4-necked flask is equipped with a blade stirrer, a bubble condenser provided with a valve for a possible distillation, a probe and a stopper (addition neck). The cobalt acetate and the iron acetate are placed with the DEG in the reaction flask and NfeCoCont_31B1 which is still warm from the previous reaction is added. The temperature is taken to 180° C. and the system is left at reflux for 3 hours. 1105 g of the product have been obtained.

Stage 3 (Product Formula: NFeCoCONT-03B3)
Reagents specifications: as above
Reagents:
Fe:Co ratio=2:1
38.12 g Co(Ac)$_{2\text{-}4}$H$_2$O (23.7% Co w/w)
Co(II)=9.036 g=0.152 moles
85.68 g Fe(CH$_3$COO)$_3$ (Sheperd pasta; c. 20% Fe w/w)
Fe(III)=17.136 g=0.308 moles
1076 g DEG
1105 g NFeCoCONT-03B2
Synthesis:

A 5 liter 4-necked flask is equipped with a blade stirrer, a bubble condenser provided with a valve for a possible distillation, a probe and a stopper (addition neck). The cobalt acetate and the iron acetate are placed with the DEG in the reaction flask and NFeCoCont_31B2 which is still warm from the previous reaction is added. The temperature is taken to 180° C. and the system is left at reflux for 3 hours. 2210 g of the product have been obtained.

Example 7

Preparation of Nanometric Cobalt Ferrite with the Growth Process According to the Present Invention Product formula: NAMA06 602
Reagents Specifications:

| | |
|---|---|
| Fe(CH$_3$COO)$_3$ | MW = 232.98 g/moles |
| Co(CH$_3$COO)$_2$•4H$_2$O | MW = 248.93 g/moles |
| Co | MW = 58.93 g/moles |
| Fe | MW = 55.85 g/moles |
| DEG | MW = 106.12 g/moles |

Reagents:
Fe:Co ratio=2:1
9.53 g Co(Ac)$_{2\text{-}4}$H$_2$O (23.7% Co w/w)
Co(II)=2.259 g=0.038 moles
21.42 g Fe(CH$_3$COO)$_3$ (Sheperd pasta; c. 20% Fe w/w)
Fe(III)=4.284 g=0.077 moles
269.04 g DEG
Synthesis:

A 4-necked flask is equipped with a blade stirrer, a bubble condenser provided with a valve for a possible distillation, a probe and a stopper (addition neck). The reagents are placed with the DEG in the reaction flask. The system is taken to the temperature of 110° C. for the solubilisation step (time: 1 h). Subsequently, the temperature is raised to 180° C. and the system is left at reflux for 5 h. The process performed while mixing leads to the formation of a black suspension.

Total obtained: g 282.

Example 8

Preparation of Nanometric Cobalt Ferrite with the Growth Process According to the Present Invention Product formula: NAMA06 601
Reagents Specifications:

| | |
|---|---|
| Fe(CH$_3$COO)$_3$ | MW = 232.98 g/moles |
| Co(CH$_3$COO)$_2$•4H$_2$O | MW = 248.93 g/moles |
| Co | MW = 58.93 g/moles |
| Fe | MW = 55.85 g/moles |
| DEG | MW = 106.12 g/moles |

Reagents:
Fe:Co ratio=2:1
9.53 g Co(Ac)$_{2\text{-}4}$H$_2$O (23.7% Co w/w)
Co(II)=2.259 g=0.038 moles
21.42 g Fe(CH$_3$COO)$_3$ (Sheperd pasta; c. 20% Fe w/w)
Fe(III)=4.284 g=0.077 moles
269.04 g DEG
Synthesis:

A 4-necked flask is equipped with a blade stirrer, a bubble condenser provided with a valve for a possible distillation, a probe and a stopper (addition neck). The reagents are placed with the DEG in the reaction flask. The system is taken to the temperature of 110° C. for the solubilisation step (time: 1 h). Subsequently, the temperature is raised to 180° C. and the system is left at reflux for 9 h. The process performed while mixing leads to the formation of a black suspension.

Total obtained: 280 g.

Example 9

Preparation of Nanometric Cobalt Ferrite with the Growth Process According to the Present Invention Product formula: NfeCo66
Reagents Specifications:

| | |
|---|---|
| Fe(CH$_3$COO)$_3$ | MW = 232.98 g/moles |
| Co(CH$_3$COO)$_2$•4H$_2$O | MW = 248.93 g/moles |
| Co | MW = 58.93 g/moles |
| Fe | MW = 55.85 g/moles |
| DEG | MW = 106.12 g/moles |

Reagents:
Fe:Co ratio=2:1
9.53 g Co(Ac)$_{2\text{-}4}$H$_2$O (23.7% Co w/w)
Co(II)=2.259 g=0.038 moles
21.42 g Fe(CH$_3$COO)$_3$ (Sheperd pasta; c. 20% Fe w/w)
Fe(III)=4.284 g=0.077 moles
269.04 g DEG
Synthesis:

A 4-necked flask is equipped with a blade stirrer, a bubble condenser provided with a valve for a possible distillation, a probe and a stopper (addition neck). The reagents are placed with the DEG in the reaction flask. The system is taken to the temperature of 110° C. for the solubilisation step (time: 1 h). Subsequently, the temperature is raised to 180° C. and the system is left at reflux for 24 hours. The process performed while mixing leads to the formation of a black suspension.

Total obtained: 280 g.

Example 10

Process for the Preparation of Cobalt Ferrite with Microwave Heating According to the Present Invention Product formula: NFeCoMW01
Reagents Specifications:

| | |
|---|---|
| $Fe(CH_3COO)_3$ | MW = 232.98 g/moles |
| $Co(CH_3COO)_2 \cdot 4H_2O$ | MW = 248.93 g/moles |
| Co | MW = 58.93 g/moles |
| Fe | MW = 55.85 g/moles |
| DEG | MW = 106.12 g/moles |

Reagents:
Fe:Co ratio=2:1
11.10 g $Co(Ac)_{2-4}H_2O$ (23.7% Co w/w)
Co(II)=2.632 g=0.0447 moles
19.23 g $Fe(CH_3COO)_3$ (Sheperd powder; c. 26% Fe w/w)
Fe(III)=4.998 g=0.0895 moles
319.67 g DEG
Synthesis:

All the reagents are placed in a 500 ml 1-neck flask. It is equipped with a bubble condenser. The flask is placed in a microwave chamber maintaining the bubble condenser outside the same. Power is applied for 7 minutes while maintaining at reflux.

Example 11

Process for the Preparation of Cobalt Ferrite with Microwave Heating According to the Present Invention Product formula: NFeCoMW03
Reagents Specifications:

| | |
|---|---|
| $Fe(CH_3COO)_3$ | MW = 232.98 g/moles |
| $Co(CH_3COO)_2 \cdot 4H_2O$ | MW = 248.93 g/moles |
| Co | MW = 58.93 g/moles |
| Fe | MW = 55.85 g/moles |
| DEG | |

Reagents:
Fe:Co ratio=2:1
11.10 g $Co(Ac)_{2-4}H_2O$ (23.7% Co w/w)
Co(II)=2.632 g=0.0447 moles
19.23 g $Fe(CH_3COO)_3$ (Sheperd powder; c. 26% Fe w/w)
Fe(III)=4.998 g=0.0895 moles
319.67 g DEG
Synthesis:

All the reagents are placed in a 500 ml 1-neck flask. It is equipped with a bubble condenser. The flask is placed in a microwave chamber maintaining the bubble condenser outside the same. Power is applied for 30 minutes while maintaining at reflux.

Example 12

Process of Preparation of Maghemite by Acetic Oxidation According to the Present Invention Product formula: Fe59.1.1.1
Reagents Specifications:

| | |
|---|---|
| $CH_3COOH$ | MW = 60.05 g/moles |
| $Fe_3O_4$(Fe74) | MW = 231.53 g/moles |
| $NaHCO_3$ | MW = 84.00 g/moles |

Reagents:
40 g $Fe_3O_4$ (Fe74) solution in DEG 0.5% w/w in $Fe_3O_4$

| | |
|---|---|
| $Fe_3O_4$ 200 mg | 0.864 mmoles |
| 1.00 g $CH_3COOH$ | 6.7 mmoles |
| 1.2 g $NaHCO_3$ | 14.3 mmoles |

Synthesis:

The magnetite solution in DEG and the acetic acid are placed in a flask provided with mixing, with a bubbling capillary and a bubble condenser. The whole is heated to 80° and is maintained at temperature for 2.5 hours.

At the end of the reaction, it is cooled to room temperature and sodium hydrogen carbonate is added. It is maintained mixing for 1 hour and the remaining solid product is then filtered. The clear dark brown solution is characterised by Mossbauer spectrometry to check the complete formation of maghemite. The solution is then evaporated in a vacuum rotary evaporator to the desired concentration.

Example 13

Functionalisation of a Cobalt Ferrite Nanoparticle with Palmitic Acid According to the Present Invention Product formula CoFe14
Reagents Specifications:

| | |
|---|---|
| Palmitic acid | MW = 256.42 g/moles |
| Et-OH | MW = 4607 g/moles |
| n-hexane | MW = 86.17 g/moles |
| $CoFe_2O_4$(:NFeCoCONT-03B3) | MW = 234.62 g/moles |

Reagents:
20 g NAMA06 solution in DEG (3% Co w/w $Fe_2O_4$)
2.56 mmoles
0.45 g palmitic acid
1.76 mmoles
40 g Et-OH
40 g n-hexane
Synthesis:

Ethanol and palmitic acid are placed in a magnetically stirred Erlenmeyer flask. It is carefully heated while mixing on a heating plate to 45-50° C. It is then maintained mixing to complete solubilisation of the palmitic acid. The nanoparticulate cobalt ferrite solution is added. The temperature settles to about 40° C. It is left mixing for 1 hour.

The content is poured from the Erlenmeyer flask in a separating funnel and hexane is extracted. The apolar phase is then washed twice with 40 ml of a diluted aqueous solution of sodium-hydrogen carbonate (0.6 g in 100 ml of water) and then with 40 ml of water. The organic phase obtained is concentrated under vacuum to the desired volume.

Example 14

Functionalisation of a Cobalt Ferrite Nanoparticle with Ethyl 12-(hydroxyamine)-12-oxododecanoate According to the Present Invention Product formula CoFe38H
Reagents Specifications:

| | |
|---|---|
| ethyl 12-(hydroxyamine)-12-oxododecanoate | MW = 273.37 g/moles |
| CoFe$_2$O$_4$(:NFeCoCONT-03B3) | MW = 234.62 g/moles |
| Buthanol | MW = 74.12 |
| Water | |

Reagents:
60 g: NFeCoCONT-03B3 solution in DEG (3% CoFe2O4 w/w) 7.67 mmoles
0.90 g ethyl 12-(hydroxyamine)-12-oxododecanoate 3.29 mmoles
120 g buthanol Synthesis:

120 g of buthanol and 0.60 g of ethyl 12-(hydroxyamine)-12-oxododecanoate are placed in a 500 ml flask (complete solubility in a few minutes). 60 g of a dispersion of cobalt ferrite nanoparticles in glycol are added to this solution and left mixing for 2 hours.

The sample has been washed with 200 g of water (formation of a double phase buthanol/water-glycol) and separated from the aqueous phase with a separating funnel. The solid product has been obtained by removing the buthanol under vacuum and then redispersing it in acetone.

Example 15

Preparation of a Construct Comprised of: Nanometric Cobalt Ferrite, PLGA and Albumin According to the Present Invention

| Product formula: NBR1 | | |
|---|---|---|
| Reagents: | Amount | Molecular weight |
| Water UP | 1000 ml | 18 d = 1.00 g/cm$^3$ |
| Acetone | 25 ml | 58.08 d = 0.79 g/cm$^3$ |
| PLGA 75/25 | 0.05 g | |
| CoFe38H | 0.02 g | |
| BSA Fraction V | 1 g | |

Synthesis:

A solution of PLGA in acetone (0.05 grams in 25 ml of acetone), a solution of BSA in ultrapure water (1 gram of BSA in 1000 ml of water) are previously prepared. 0.4 ml of a 5% CoFe38H suspension in acetone (w/V) are added to the PLGA solution.

A double peristaltic pump is provided to continuously add the acetonic solution (containing PLGA and CoFe38H) in a water flow containing BSA (volume ratio acetone/water=1/40). The corresponding immersion tubes withdraw the solution directly from the reservoirs containing the two solutions.

The pumping ratio of the two peristaltic pumps is set to 1/40 so that the two solutions are consumed at the same time. The product of the final mixing is collected in a graduated cylinder. The pumping rate is set so that the mixing of the solutions occurs in 10 minutes.

The resulting final solution is treated under vacuum so as to completely remove acetone. The resulting final solution is concentrated under high-vacuum at T<45° C. or by means of ultrafiltration until the desired concentration is obtained.

Size Characterisation by Means of DLS

| Sample | Solvent | PDI | Average diameter | Attenuation |
|---|---|---|---|---|
| NBR1 | Water solution | 0.16 | 190 | 7-380 |

Example 16

Preparation of a Construct Comprising: Nanometric Cobalt Ferrite, Paclitaxel, PLGA and Albumin According to the Present Invention Product formula: NBR1F1

| Reagents: | Amount | Molecular weight |
|---|---|---|
| UP water | 956 ml | 18 d = 1.00 g/cm$^3$ |
| Acetone | 104 ml | 58.08 d = 0.79 g/cm$^3$ |
| PLGA 75/25 | 0.5 g | |
| CoFe38H | 0.2 g | |
| BSA Fraction V | 1 g | |
| Paclitaxel | 10 mg | 853.91 |

Synthesis:

A solution of PLGA in acetone (0.5 grams in 100 ml of acetone) and a solution of BSA in ultrapure water (1 gram of BSA in 800 ml of water) are previously prepared. 10 mg of Paclitaxel and 4 ml of a 5% CoFe38H suspension in acetone (w/V) are added to the PLGA solution in acetone.

A double peristaltic pump is provided to continuously add the acetonic solution (containing PLGA, CoFe38H and Paclitaxel) in a water flow containing BSA (volume ratio acetone/water=1/8). The corresponding immersion tubes withdraw the solution directly from the reservoirs containing the two solutions. The pumping ratio of the two peristaltic pumps is set to 1/8 so that the two solutions are consumed at the same time. The product of the final mixing is collected in a graduated cylinder. The pumping rate is set so that the mixing of the solutions occurs in 10 minutes.

The resulting final solution is treated under vacuum to completely remove acetone.

The resulting final solution is concentrated under high-vacuum at T<45° C. or by means of ultrafiltration until the desired concentration is obtained.

Example 17

Preparation of a Construct Comprising: Nanometric Cobalt Ferrite, 9-nitro-camptothecin, PLGA and Albumin According to the Present Invention Product formula: NBR1F2

| Reagents: | Amount | Molecular weight |
|---|---|---|
| UP water | 1356 ml | 18 d = 1.00 g/cm$^3$ |
| Acetone | 104 ml | 58.08 d = 0.79 g/cm$^3$ |
| PLGA 75/25 | 0.5 g | |
| CoFe38H | 0.2 g | |
| BSA Fraction V | 1 g | |
| NaCl | 14.4 g | 58.44 |
| 9-nitro-camptothecin | 25 mg | |
| Glutaraldehyde | 1.56 mg | 100.1 |

Synthesis:

A solution of PLGA in acetone (0.5 grams in 100 ml of acetone) and a solution of BSA in ultrapure water (1 gram of BSA in 800 ml of water) are previously prepared. 25 mg of 9-nitro-camptothecin and 4 ml of a 5% CoFe38H suspension in acetone (w/V) are added to the PLGA solution in acetone.

A double peristaltic pump is provided to continuously add the acetonic solution (containing PLGA, CoFe38H and 9-nitro-camptothecin) in a water flow containing BSA (volume ratio acetone/water=1/8). The corresponding immersion tubes withdraw the solution directly from the reservoirs containing the two solutions. The pumping ratio of the two peristaltic pumps is set to 1/8 so that the two solutions are consumed at the same time. The product of the final mixing is collected in a graduated cylinder, in which there are already 400 ml of water containing 3.6% of NaCl. The pumping rate is set so that the mixing of the solutions occurs in 10 minutes.

The resulting final solution is treated under vacuum to completely remove acetone.

Subsequently, 156 ml of an aqueous solution of glutaraldehyde (conc. 10 mg/l of Glutaraldehyde) are added and it is left to rest for 10 h.

The resulting final solution is concentrated under high-vacuum at T<45° C. or by means of ultrafiltration until the desired concentration is obtained.

Example 18

Preparation of a Construct Comprising Nanometric Cobalt Ferrite and a Block Polymer According to the Present Invention Product formula: NBR2

| Reagents: | Amount | Molecular weight |
|---|---|---|
| UP water | 400 ml | 18 d = 1.00 g/cm$^3$ |
| Acetone | 200 g | 58.08 d = 0.79 g/cm$^3$ |
| CoFe38H | 1 g | |
| Pluronics F-68 | 5.6 g | |

Synthesis:

A solution of CoFe38H in acetone (1 gram in 200 ml of acetone) is previously prepared.

A double peristaltic pump is provided to continuously add the acetonic solution (containing CoFe38H) in a water flow containing Pluronics F-68 (volume ratio acetone/water=1/2). The corresponding immersion tubes withdraw the solution directly from the reservoirs containing the two solutions. The pumping ratio of the two peristaltic pumps is set to 1/2 so that the two solutions are consumed at the same time. The pumping rate is set so that the mixing of the solutions occurs in 10 minutes.

The resulting final solution is treated under vacuum to completely remove acetone.

Size Characterisation by Means of DLS

| Sample | Solvent | PDI | Average diameter | Attenuation |
|---|---|---|---|---|
| NBR2 | Physiological solution | 0.15 | 66 | 7-240 |

The DLS confirms the stability of the nanoparticles in aqueous solution and in physiological solution.

The raw image analysis shows very, distinct dark cores of about 17-45 nm in the case of STEM, the separations are clear-cut and on the average equal to about 5-15 nm (surfactant layer).

Example 19

Preparation of a Construct Comprising: Nanometric Cobalt Ferrite, Cis-diamminoplatinum (II) Dichloride, PLGA and Albumin According to the Present Invention Product formula: Product formula: NBR1F3

| Reagents: | Amount | Molecular weight |
|---|---|---|
| UP water | 1356 ml | 18 d = 1.00 g/cm$^3$ |
| Acetone | 104 ml | 58.08 d = 0.79 g/cm$^3$ |
| PLGA 75/25 | 0.5 g | |
| CoFe38H | 0.2 g | |
| BSA Fraction V | 1 g | |
| NaCl | 14.4 g | 58.44 |
| cis-diammineplatinum (II) dichloride | 100 mg | 300.1 |

Synthesis:

a PLGA solution in acetone (0.5 grams in 100 ml of acetone);
a BSA solution in ultrapure water (1 gram of BSA in 800 ml of water);
a NaCl solution in ultrapure water (14.4 g of NaCl in 400 ml of water) are previously prepared.

4 ml of a 5% CoFe38H suspension in acetone (w/V) are added to the PLGA solution in acetone, while 100 mg of cis-diammineplatinum (II) dichloride are dissolved in the albumin aqueous solution.

A double peristaltic pump is provided to continuously add the acetonic solution (containing PLGA and CoFe38H) in a water flow containing BSA and the drug (volume ratio acetone/water=1/8). The corresponding immersion tubes withdraw the solution directly from the reservoirs containing the two solutions.

The pumping ratio of the two peristaltic pumps is set to 1/8 so that the two solutions are consumed at the same time. The product of the final mixing is collected in a graduated cylinder, in which there are already 400 ml of water containing 3.6% of NaCl. The pumping rate is set so that the mixing of the solutions occurs in 10 minutes.

The resulting final solution is concentrated under high-vacuum at T<45° C. or by means of ultrafiltration until the desired concentration is obtained.

Example 20

Preparation of a Construct Comprising Nanometric Cobalt Ferrite, Paclitaxel and a Block Polymer Product formula: NBR2F1

| Reagents: | Amount | Molecular weight |
|---|---|---|
| Water | 80 ml | 18 d = 1.00 g/cm$^3$ |
| Acetone | 40 g | 58.08 d = 0.79 g/cm$^3$ |
| CoFe38H | 0.2 g | |
| Pluronics F-68 | 1.12 g | |
| Paclitaxel | 10 mg | 853.9 |

Synthesis:

A solution of CoFe38H in acetone (0.2 grams in 40 ml of acetone) is previously prepared and 10 mg of Paclitaxel are solubilised in the mixture.

A double peristaltic pump is provided to continuously add the acetonic solution (containing CoFe38H and the drug) in a water flow containing Pluronics F-68 (volume ratio acetone/water=1/2). The corresponding immersion tubes withdraw the solution directly from the reservoirs containing the two solutions. The pumping ratio of the two peristaltic pumps is set to 1/2 so that the two solutions are consumed at the same time. The pumping rate is set so that the mixing of the solutions occurs in 6 minutes.

The resulting final solution is treated under vacuum so as to completely remove acetone.

Size Characterisation by Means of DLS

| Sample | Solvent | PDI | Average diameter | Attenuation |
|---|---|---|---|---|
| NBR2F1 | Physiological solution | 0.12 | 52 | 7-310 |

The DLS confirms the stability of the nanoparticles in aqueous solution and in physiological solution.

Example 21

Preparation of the Construct Comprising Nanometric Magnetite and a Water-Soluble Polyamineamide Polymer (BAC-EDDA) of Formula (A) According to the Present Invention Product formula: NBR4

| Reagents: | Amount | Molecular weight |
|---|---|---|
| Water | 200 ml | 18 d = 1.00 g/cm$^3$ |
| Diethylene glycol | 40 g | 106.1 d = 1.12 g/cm$^3$ |
| Fe77 | 0.2 g | |
| BAC-EDDA polymer | 1.12 g | |

Water-soluble stealth polymer based on ethylene diamine diacetic acid

Synthesis:

a solution of magnetite in diethylene glycol (0.2 grams in 40 ml of solvent);

a solution of BAC-EDDA polymer in water (1.12 grams in 200 ml of solvent) are previously prepared;

A double peristaltic pump is provided to continuously add the organic solution (containing magnetite) in a water flow containing the BAC-EDDA polymer (volume ratio diethylene glycol/water=1/5). The corresponding immersion tubes withdraw the solution directly from the reservoirs containing the two solutions. The pumping ratio of the two peristaltic pumps is set to 1/5 so that the two solutions are consumed at the same time. The pumping rate is set so that the mixing of the solutions occurs in 12 minutes.

The resulting final solution is dialysed with ultrapure water so as to remove most of the organic solvent and obtain a solution containing at most 0.1% diethylene glycol.

Size Characterisation by Means of DLS

| Sample | Solvent | PDI | Average diameter | Attenuation |
|---|---|---|---|---|
| NBR4 | Physiological solution | 0.19 | 41 | 7-340 |

The DLS confirms the stability of the nanoparticles in aqueous solution and in physiological solution.

Example 22

Preparation of a Construct Comprising Nanometric Magnetite, a Water-Soluble Polymer (BAC-EDDA) and Cis-diammineplatinum (II) Dichloride According to the Present Invention Product formula: NBR4F1

| Reagents: | Amount | Molecular weight |
|---|---|---|
| Water | 200 ml | 18 d = 1.00 g/cm$^3$ |
| Diethylene glycol | 40 g | 106.1 d = 1.12 g/cm$^3$ |
| Fe77 | 0.2 g | |
| BAC-EDDA polymer | 1.12 g | |
| Cis-diammineplatinum (II) dichloride | 100 mg | 300.1 |

Water-soluble stealth polymer based on ethylene diamine diacetic acid

Synthesis:

a solution of magnetite in diethylene glycol (0.2 grams in 40 ml of solvent);

a solution of BAC-EDDA polymer in water (1.12 grams in 200 ml of solvent) in which 100 mg of Cis-Diammineplatinum (II) dichloride are previously prepared;

A double peristaltic pump is provided to continuously add the organic solution (containing magnetite) in a water flow containing the BAC-EDDA polymer and the Cis-Diammineplatinum (II) dichloride (volume ratio diethylene glycol/water=1/5). The corresponding immersion tubes withdraw the solution directly from the reservoirs containing the two solutions. The pumping ratio of the two peristaltic pumps is set to 1/5 so that the two solutions are consumed at the same time. The pumping rate is set so that the mixing of the solutions occurs in 8 minutes.

The resulting final solution is dialysed with ultrapure water so as to remove most of the organic solvent and to obtain a solution containing at most 0.1% diethylene glycol.

Size Characterisation by Means of DLS

| Sample | Solvent | PDI | Average diameter | Attenuation |
|---|---|---|---|---|
| NBR3F1 | Physiological solution | 0.14 | 52 | 7-320 |

The DLS confirms the stability of the nanoparticles in aqueous solution and in physiological solution.

Example 23

Preparation of a Construct Comprising of Nanometric Cobalt Ferrite, PLGA and a Block Polymer According to the Present Invention Product formula: NBR32

| Reagents: | Amount | Molecular weight |
|---|---|---|
| UP water | 800 ml | 18 d = 1.00 g/cm³ |
| Acetone | 20 g | 58.08 d = 0.79 g/cm³ |
| CoFe38H | 0.02 g | |
| PLGA | 0.05 g | |
| Pluronics F-68 | 0.8 g | |

Synthesis:

A solution of PLGA in acetone (0.05 grams in 20 ml of acetone), a solution of Pluronic F-68 in ultrapure water (0.8 gram of PLURONIC F-68 in 800 ml of water) are previously prepared. 0.4 ml of a 5% CoFe38H suspension in acetone (w/V) are added to the PLGA solution.

A double peristaltic pump is provided to continuously add the acetonic solution (containing PLGA and CoFe38H) in a water flow containing PLURONIC F-68 (volume ratio acetone/water=1/40). The corresponding immersion tubes withdraw the solution directly from the reservoirs containing the two solutions.

The pumping ratio of the two peristaltic pumps is set to 1/40 so that the two solutions are consumed at the same time. The product of the final mixing is collected in a graduated cylinder. The pumping rate is set so that the mixing of the solutions occurs in 10 minutes.

The resulting final solution is treated under vacuum so as to completely remove acetone. The resulting final solution is concentrated under high-vacuum at T-<45° C. or by means of ultrafiltration until the desired concentration is obtained.

Example 24

Preparation of a Construct Comprising of Nanometric Cobalt Ferrite, PLGA and a Block Polymer According to the Present Invention Product formula: NBR5

| Reagents: | Amount | Molecular weight |
|---|---|---|
| UP water | 800 ml | 18 d = 1.00 g/cm³ |
| Ethanol | 20 g | |
| CoFe38H | 0.02 g | |
| Colesterol | 0.05 g | |
| Pluronics F-68 | 0.8 g | |

Synthesis:

A solution of cholesterol in ethanol (0.05 grams in 20 ml of acetone), a solution of Pluronic F-68 in ultrapure water (0.8 gram of PLURONIC F-68 in 800 ml of water) are previously prepared. 0.4 ml of a 5% CoFe38H suspension in acetone (w/V) are added to the cholesterol solution.

A double peristaltic pump is provided to continuously add the acetonic solution (containing cholesterol and CoFe38H) in a water flow containing PLURONIC F-68 (volume ratio acetone/water=1/40). The corresponding immersion tubes withdraw the solution directly from the reservoirs containing the two solutions.

The pumping ratio of the two peristaltic pumps is set to 1/40 so that the two solutions are consumed at the same time. The product of the final mixing is collected in a graduated cylinder. The pumping rate is set so that the mixing of the solutions occurs in 10 minutes.

The resulting final solution is treated under vacuum so as to completely remove acetone. The resulting final solution is concentrated under high-vacuum at T<45° C. or by means of ultrafiltration until the desired concentration is obtained. Moreover, for completeness, example of preparation of some polymers useful for the invention as above said are reported hereinafter.

Example 23

Synthesis of BAC-EDDS

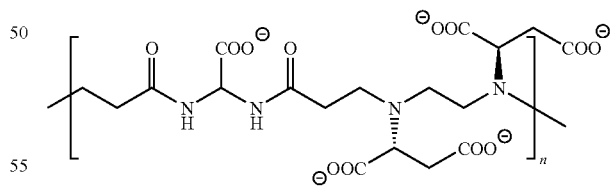

Lithium hydroxide monohydrate (112.64 mg, 2.6576 mmol) was added under stirring to a 37.36% solution (as determined titrimetrically just before use) of (S,S)-ethylenediamine-N,N'-disuccinic acid trisodium salt (EDDS) (2 ml, 2.6576 mmol) contained in a 50 ml 2 necked flask. 2,2-Bis-acrylamidoacetic acid (BAC) (530.6 mg, 2.6576 mmol) and lithium hydroxide monohydrate (112.64 mg, 2.6576 mmol) were then added and the reaction mixture was maintained 7 days under stirring at 18-20° C. After this time, 2-propanol (25 ml) was added. The crude product was isolated by centrifuging, extracted with fresh 2-propanol (2×15 ml) and ether (1×15 ml) and finally dried to constant weight at room T° and 0.1 tor. Yield 61.28%. $\overline{M}_w$=6900, $\overline{M}_n$=5300.

Example 24

Synthesis of BP-EDDS

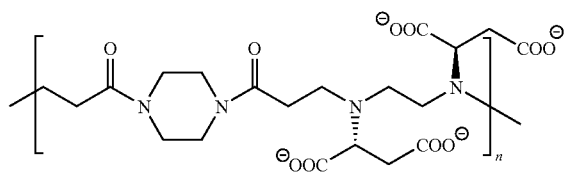

Lithium hydroxide monohydrate (112.64 mg, 2.6576 mmol) was added under stirring to a 37.36% solution (as determined titrimetrically just before use) of EDDS) (2 ml, 2.6576 mmol) contained in a 50 ml 2 necked flask. 1,4-bisacryloylpiperazine (BP) (516.19 mg. 2.6576 mmol) was then added. The reaction mixture was then treated and the final product isolated exactly as described in the previous case. Yield 91.8%. $\overline{M}_w$=6500, $\overline{M}_n$=4500.

Synthesis of BA-EDDS

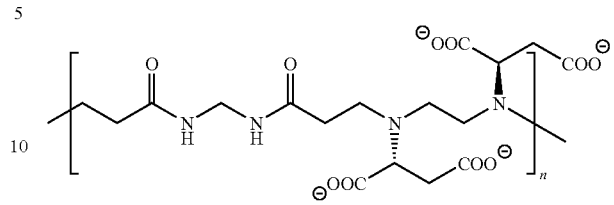

Lithium hydroxide monohydrate (112.64 mg, 2.6576 mmol) was added under stirring to a 37.36% solution (as determined titrimetrically just before use) of EDDS) (2 ml, 2.6576 mmol) contained in a 50 ml 2 necked flask. N,N'methylenebisacrylamide (MBA) (516.19 mg, 2.6576 mmol) was then added and the reaction mixture stirred at room temperature for 2 days. After this time, of water (1.5 ml) was added to the cloudy mixture that was gently warmed to dissolve the suspended materials.

The reaction mixture was then treated and the final product isolated exactly as described in the previous case. Yield 90.1%. $\overline{M}_w$=2600, $\overline{M}_n$=1900.

TABLE 1(a)

synthesis of non-functionalised magnetic nanoparticles

| Formula | Reagents (moles) | | | | | | | SYNTHESIS | | | |
| | Fe III acet. | Fe II acet. | Co II acet. | Ni II acet. | Zn II acet. | Mn II acet. | Cr III acet. | Type of synthesis | Cycles | Time* | Described example |
|---|---|---|---|---|---|---|---|---|---|---|---|
| FeDoCo01 | 0.04 | 0.019 | 0.001 | | | | | BR | — | — | |
| FeDoCr01 | 0.039 | 0.02 | | | | | 0.001 | BR | — | — | |
| FeDoMn01 | 0.04 | 0.019 | | | | 0.001 | | BR | — | — | |
| FeDoNi01 | 0.04 | 0.019 | | 0.001 | | | | BR | — | — | |
| FeDoNi03 | 0.04 | 0.015 | | 0.005 | | | | BR | — | — | 3 |
| FeDoZn01 | 0.04 | 0.019 | | | 0.001 | | | BR | — | — | |
| Fe74 | 0.04 | 0.02 | | | | | | BR | — | — | 2 |
| NFeCo31 | 0.04 | | 0.02 | | | | | BR | — | — | 1 |
| NFeNi03 | 0.04 | | | | | | 0.02 | BR | — | — | |
| NFeCoCONT-04B9 | 0.04 | | 0.02 | | | | | CO | 9 | — | |
| NFeCoCONT-03B1 | 0.04 | | 0.02 | | | | | CO | 1 | — | 6 |
| NFeCoCONT-03B2 | 0.04 | | 0.02 | | | | | CO | 2 | — | 6 |
| NFeCoCONT-03B3 | 0.04 | | 0.02 | | | | | CO | 3 | — | 6 |
| NFeCoMW01 | 0.04 | | 0.02 | | | | | MO | — | 7 | 10 |
| NFeCoMW02 | 0.04 | | 0.02 | | | | | MO | — | 10 | |
| NFeCoMW03 | 0.04 | | 0.02 | | | | | MO | — | 30 | 11 |
| NFeCoMW04 | 0.04 | | 0.02 | | | | | MO | — | 6 | |
| NFeCoMW05 | 0.04 | | 0.02 | | | | | MO | — | 8 | |
| NFeCoMW06 | 0.04 | | 0.02 | | | | | MO | — | 38 | |
| FeDoCo02 | 0.04 | 0.018 | 0.002 | | | | | RI | 1 | — | |
| FeDoCo03 | 0.04 | 0.015 | 0.005 | | | | | RI | 2 | — | |
| FeDoCr02 | 0.038 | 0.02 | | | | | 0.002 | RI | 1 | — | |
| FeDoCr03 | 0.035 | 0.02 | | | | | 0.005 | RI | 2 | — | |
| FeDoMn02 | 0.04 | 0.018 | | | | 0.002 | | RI | 1 | — | |
| FeDoMn03 | 0.04 | 0.015 | | | | 0.005 | | RI | 2 | — | |
| FeDoNi02 | 0.04 | 0.018 | | 0.002 | | | | RI | 1 | — | |
| FeDoZn02 | 0.04 | 0.018 | | | 0.002 | | | RI | 1 | — | |
| FeDoZn03 | 0.04 | 0.015 | | | 0.005 | | | RI | 2 | — | |
| Fe70 | 0.04 | 0.02 | | | | | | RI | 5 | — | |
| Fe75 | 0.04 | 0.02 | | | | | | RI | 1 | — | 5 |
| Fe76 | 0.04 | 0.02 | | | | | | RI | 2 | — | 5 |
| Fe77 | 0.04 | 0.02 | | | | | | RI | 3 | — | |
| Fe78 | 0.04 | 0.02 | | | | | | RI | 4 | — | |
| NFeCo35 | 0.04 | | 0.02 | | | | | RI | 1 | — | 4 |
| NFeCo36 | 0.04 | | 0.02 | | | | | RI | 2 | — | 4 |
| NFeCo38 | 0.04 | | 0.02 | | | | | RI | 3 | — | |
| NFeCo42 | 0.04 | | 0.02 | | | | | RI | 4 | — | |

TABLE 1(a)-continued synthesis of non-functionalised magnetic nanoparticles

| Formula | Fe III acet. | Fe II acet. | Co II acet. | Ni II acet. | Zn II acet. | Mn II acet. | Cr III acet. | Type of synthesis | Cycles | Time* | Described example |
|---|---|---|---|---|---|---|---|---|---|---|---|
| NFeCo44 | 0.04 | | 0.02 | | | | | RI | 5 | — | |
| NAMA06 | 0.04 | | 0.02 | | | | | ST | — | 4 | |
| NAMA06 602 | 0.04 | | 0.02 | | | | | ST | — | 5 | 7 |
| NAMA06 601 | 0.04 | | 0.02 | | | | | ST | — | 9 | 8 |
| NFeCo66 | 0.04 | | 0.02 | | | | | ST | — | 24 | 9 |

PTTIT 7001: BR
semicontinuous substitution method CO
Microwave method: MO
continuous process: RI
growth method: ST
*time in minutes (MO) or hours (ST)

TABLE 1(b)

Indirect synthesis of magnetic nanoparticles

| Formula | Solvent | Oxidant | Reaction t | precursor | Described example |
|---|---|---|---|---|---|
| Fe59.1.1.1 | CH3COOH | O2 | 2.5 h | Fe74 | 12 |
| Fe59.1.1.2 | CH3COOH | O2 | 2.5 h | Fe75 | |
| Fe59.1.1.4 | CH3COOH | O2 | 2.5 h | Fe76 | |
| Fe59.1.1.5 | CH3COOH | O2 | 2.5 h | Fe77 | |
| Fe59.1.1.3 | CH3COOH | O2 | 2.5 h | Fe78 | |

TABLE 1(c)

Functionalisation of the magnetic nanoparticles

| Formula | precursor | Functionalisation | SYNTHESIS | Described example |
|---|---|---|---|---|
| Fe70.AK.1 | FE70 | C16-phosphate | see PCT Appln. PCT/EP2007/050036 | |
| CoFe14 | NFeCoCONT-03B3 | Palmitic acid | see PCT Appln. PCT/EP2007/050036 | 13 |
| CoFe17 | NAMA06 | C16-phosphate | see PCT Appln. PCT/EP2007/050036 | |
| CoFe17OL | NAMA06 | Oleic acid | see PCT Appln. PCT/EP2007/050036 | |
| CoFe25 | NAMA06 | C12-Hydroxyam.-OH | see PCT Appln. PCT/EP2007/050036 | |
| CoFe31 | NAMA06 | NHOHCOC12-NH2 | see PCT Appln. PCT/EP2007/050036 | |
| CoFe38 | NFeCoCONT-03B1 | NHOHCOC12-COOR | see PCT Appln. PCT/EP2007/050036 | |
| CoFe38H | NFeCoCONT-03B3 | NHOHCOC12-COOR | see PCT Appln. PCT/EP2007/050036 | 14 |
| CoFe8H | NFeCocont-04B9 | C16-Hydroxyam. | see PCT Appln. PCT/EP2007/050036 | |
| CoFe42ANF | NFeCo42 | C16-phosphate | see PCT Appln. PCT/EP2007/050036 | |

TABLE 1(d)

CONSTRUCTS

| Formula | precursor | Coating of the metal oxide | Polymer | Surface agent | Drug | Described example |
|---|---|---|---|---|---|---|
| NBR1 | CoFe38H | NHOHCOC12—COOR | PLGA | BSA | none | 15 |
| NBR2 | CoFe38H | NHOHCOC12—COOR | Pluronic | none | none | 18 |
| NBR3 | Fe77 | none | BAC-EDDA polymer | none | none | 21 |
| NBRF1 | CoFe38H | NHOHCOC12—COOR | PLGA | BSA | Paclitaxel | 16 |
| NBRF2 | CoFe38H | NHOHCOC12—COOR | PLGA | BSA | 9-nitro Camptothecin | 17 |
| NBRF3 | CoFe38H | NHOHCOC12—COOR | PLGA | BSA | Cis-Diammine platinum (II) dichloride | 19 |
| NBRF4 | CoFe38H | NHOHCOC12—COOR | Pluronic | none | Paclitaxel | 20 |
| NBRF5 | Fe77 | none | BAC-EDDA polymer | none | Cis-Diammine platinum (II) dichloride | 22 |

TABLE 2

(Particle size)

| Formula | Oxide | Synthesis | Particle size (nm) | PDI |
|---|---|---|---|---|
| Fe59.1.1.1 | Maghemite | OX | 5.73 | 0.25 |
| Fe59.1.1.2 | Maghemite | OX | 7.53 | 0.13 |
| Fe59.1.1.3 | Maghemite | OX | 19.2 | 0.18 |
| Fe59.1.1.4 | Maghemite | OX | 9.72 | 0.21 |
| Fe59.1.1.5 | Maghemite | OX | 14.1 | 0.19 |
| Fe Do Co 01 | Magnetite (d Co) | BR | 38.6 | 0.21 |
| Fe Do Cr 01 | Magnetite (d Cr) | BR | 40 | 0.19 |
| Fe Do Mn 01 | Magnetite (d Mn) | BR | 39.8 | 0.14 |
| Fe Do Ni 01 | Magnetite (d Ni) | BR | 36.9 | 0.22 |
| Fe Do Ni 03 | Magnetite (d Ni) | BR | 40 | 0.18 |
| Fe Do Zn 01 | Magnetite (d Zn) | BR | 43.2 | 0.18 |
| Fe74 | Magnetite | BR | 40.3 | 0.22 |
| NFeCo31 | Cobalt Ferrite | BR | 7.46 | 0.18 |
| NFeNi03 | Nickel Ferrite | BR | 9.7 | 0.25 |
| NFeCoCONT-03B1 | Cobalt Ferrite | CO | 9.2 | 0.18 |
| NFeCoCONT-03B2 | Cobalt Ferrite | CO | 11.5 | 0.16 |
| NFeCoCONT-03B3 | Cobalt Ferrite | CO | 14.63 | 0.13 |
| NfeCocont-04B9 | Cobalt Ferrite | CO | 36 | 0.14 |
| NFeCoMW01 | Cobalt Ferrite | MO | 90 | 0.21 |
| NFeCoMW02 | Cobalt Ferrite | MO | 100 | 0.18 |
| NFeCoMW03 | Cobalt Ferrite | MO | 28 | 0.43 |
| NFeCoMW04 | Cobalt Ferrite | MO | 87 | 0.22 |
| NFeCoMW05 | Cobalt Ferrite | MO | 101 | 0.27 |
| NFeCoMW06 | Cobalt Ferrite | MO | 80 | 0.19 |
| Fe Do Co 02 | Magnetite (d Co) | RI | 41.2 | 0.18 |
| Fe Do Co 03 | Magnetite (d Co) | RI | 40.6 | 0.23 |
| Fe Do Cr 02 | Magnetite (d Cr) | RI | 40.9 | 0.26 |
| Fe Do Cr 03 | Magnetite (d Cr) | RI | 41.2 | 0.19 |
| Fe Do Mn 02 | Magnetite (d Mn) | RI | 42.6 | 0.16 |
| Fe Do Mn 03 | Magnetite (d Mn) | RI | 41.1 | 0.16 |
| Fe Do Ni 02 | Magnetite (d Ni) | RI | 39.6 | 0.19 |
| Fe Do Zn 02 | Magnetite (d Zn) | RI | 42.6 | 0.23 |
| Fe Do Zn 03 | Magnetite (d Zn) | RI | 43.2 | 0.2 |
| Fe70 | Magnetite | RI | 68.8 | 0.13 |
| Fe75 | Magnetite | RI | 32.7 | 0.2 |
| Fe76 | Magnetite | RI | 37.8 | 0.19 |
| Fe77 | Magnetite | RI | 43.8 | 0.16 |
| Fe78 | Magnetite | RI | 57.8 | 0.23 |
| NFeCo35 | Cobalt Ferrite | RI | 9.09 | 0.13 |
| NFeCo36 | Cobalt Ferrite | RI | 11.2 | 0.2 |
| NFeCo38 | Cobalt Ferrite | RI | 13.36 | 0.09 |
| NFeCo42 | Cobalt Ferrite | RI | 16 | 0.11 |
| NFeCo44 | Cobalt Ferrite | RI | 22 | 0.06 |
| NAMA06 | Cobalt Ferrite | ST | 16 | 0.19 |
| NAMA06 602 | Cobalt Ferrite | ST | 18.94 | 0.13 |
| NAMA06 601 | Cobalt Ferrite | ST | 33 | 0.16 |
| NFeCo66 | Cobalt Ferrite | ST | 137.87 | 0.18 |

TABLE 3

(hyperthermic effect of the non-functionalised nanoparticles)

| Formula | Oxide | Synthesis | Particle size (nm) | Hyperthermic effect (° C.) |
|---|---|---|---|---|
| Fe59.1.1.1 | Maghemite | OX | 5.73 | 0.3 |
| Fe59.1.1.2 | Maghemite | OX | 7.53 | 3.6 |
| Fe59.1.1.3 | Maghemite | OX | 19.2 | 5.8 |
| Fe59.1.1.4 | Maghemite | OX | 9.72 | 3.7 |
| Fe59.1.1.5 | Maghemite | OX | 14.1 | 4.6 |
| Fe Do Co 01 | Magnetite (d Co) | BR | 38.6 | 1.8 |
| Fe Do Cr 01 | Magnetite (d Cr) | BR | 40 | 2 |
| Fe Do Mn 01 | Magnetite (d Mn) | BR | 39.8 | 1.3 |
| Fe Do Ni 01 | Magnetite (d Ni) | BR | 36.9 | 1.6 |
| Fe Do Ni 03 | Magnetite (d Ni) | BR | 40 | 0.9 |
| Fe Do Zn 01 | Magnetite (d Zn) | BR | 43.2 | 1.4 |
| Fe74 | Magnetite | BR | 40.3 | 7 |
| NFeCo31 | Cobalt Ferrite | BR | 7.46 | 2.2 |
| NFeNi03 | Nickel Ferrite | BR | 9.7 | 0.2 |
| NFeCoCONT-03B1 | Cobalt Ferrite | CO | 9.2 | 5.3 |
| NFeCoCONT-03B2 | Cobalt Ferrite | CO | 11.5 | 13.1 |
| NFeCoCONT-03B3 | Cobalt Ferrite | CO | 14.63 | 30.2 |
| NfeCocont-04B9 | Cobalt Ferrite | CO | 36 | 41.4 |
| NFeCoMW01 | Cobalt Ferrite | MO | 90 | 7.7 |
| NFeCoMW02 | Cobalt Ferrite | MO | 100 | 8.1 |
| NFeCoMW03 | Cobalt Ferrite | MO | 28 | 1.2 |
| NFeCoMW04 | Cobalt Ferrite | MO | 87 | 3.9 |
| NFeCoMW05 | Cobalt Ferrite | MO | 101 | 7.9 |
| NFeCoMW06 | Cobalt Ferrite | MO | 80 | 3.7 |
| Fe Do Co 02 | Magnetite (d Co) | RI | 41.2 | 1.6 |
| Fe Do Co 03 | Magnetite (d Co) | RI | 40.6 | 1.9 |
| Fe Do Cr 02 | Magnetite (d Cr) | RI | 40.9 | 1.8 |
| Fe Do Cr 03 | Magnetite (d Cr) | RI | 41.2 | 2.3 |
| Fe Do Mn 02 | Magnetite (d Mn) | RI | 42.6 | 0.9 |
| Fe Do Mn 03 | Magnetite (d Mn) | RI | 41.1 | 1.1 |
| Fe Do Ni 02 | Magnetite (d Ni) | RI | 39.6 | 2.1 |
| Fe Do Zn 02 | Magnetite (d Zn) | RI | 42.6 | 2.1 |
| Fe Do Zn 03 | Magnetite (d Zn) | RI | 43.2 | 2 |
| Fe70 | Magnetite | RI | 68.8 | 3.1 |
| Fe75 | Magnetite | RI | 32.7 | 4.5 |
| Fe76 | Magnetite | RI | 37.8 | 12.2 |
| Fe77 | Magnetite | RI | 43.8 | 10.1 |
| Fe78 | Magnetite | RI | 57.8 | 14.5 |
| NFeCo35 | Cobalt Ferrite | RI | 9.09 | 4.3 |
| NFeCo36 | Cobalt Ferrite | RI | 11.2 | 11.2 |
| NFeCo38 | Cobalt Ferrite | RI | 13.36 | 21.8 |
| NFeCo42 | Cobalt Ferrite | RI | 16 | 49.6 |
| NFeCo44 | Cobalt Ferrite | RI | 22 | 64.1 |
| NAMA06 | Cobalt Ferrite | ST | 16 | 9.3 |
| NAMA06 602 | Cobalt Ferrite | ST | 18.94 | 13.3 |
| NAMA06 601 | Cobalt Ferrite | ST | 33 | 20 |
| NFeCo66 | Cobalt Ferrite | ST | 137.87 | 1 |

TABLE 4

(hyperthermic effect of the functionalised particles and constructs)

| Product formula | precursor | Oxide | Functionalis. of the particles | Polymer | Surface agent | Drug | Dispersion means | Conc. in metal oxide (%) | Hyperthermia of the precursor (normalised at 1%) | Hyperthermia of the product (normalised at 1%) |
|---|---|---|---|---|---|---|---|---|---|---|
| CoFe14 | NFeCoCONT-03B3 | Cobalt ferrite | Palmitic acid | none | none | none | hexane | 0.5 | 10.07 | 12.80 |
| CoFe17 | NAMA06 | Cobalt ferrite | C16-phosphate | none | none | none | hexane | 1.5 | 3.10 | 4.93 |
| CoFe17 | NAMA06 | Cobalt ferrite | C16-phosphate | none | none | none | paraffin | 1.5 | 3.10 | 3.47 |
| CoFe17OL | NAMA06 | Cobalt ferrite | Oleic acid | none | none | none | hexane | 0.5 | 3.10 | 4.60 |

TABLE 4-continued (hyperthermic effect of the functionalised particles and constructs)

| Product formula | precursor | Oxide | Functionalis. of the particles | Polymer | Surface agent | Drug | Dispersion means | Conc. in metal oxide (%) | Hyperthermia of the precursor (normalised at 1%) | Hyperthermia of the product (normalised at 1%) |
|---|---|---|---|---|---|---|---|---|---|---|
| CoFe25 | NAMA06 | Cobalt ferrite | C12-Hydroxyam.-OH | none | none | none | paraffin | 1.5 | 3.10 | 3.13 |
| CoFe31 | NAMA06 | Cobalt ferrite | NHOHCOC12—NH2 | none | none | none | water | 0.5 | 3.10 | 1.00 |
| CoFe31 | NAMA06 | Cobalt ferrite | NHOHCOC12—NH2 | none | none | none | DEG | 1.5 | 3.10 | 2.80 |
| CoFe38 | NFeCoCONT-03B1 | Cobalt ferrite | NHOHCOC12—COOR | none | none | none | buthanol | 1.5 | 1.77 | 1.33 |
| CoFe38H | NFeCoCONT-03B3 | Cobalt ferrite | NHOHCOC12—COOR | none | none | none | acetone | 3 | 10.07 | 11.07 |
| CoFe38H | NFeCoCONT-03B3 | Cobalt ferrite | NHOHCOC12—COOR | none | none | none | DEG | 3 | 10.07 | 10.47 |
| CoFe42ANF | NFeCo42 | Cobalt ferrite | C16-phosphate | none | none | none | hexane | 1 | 16.53 | 35.20 |
| CoFe42ANF | NFeCo42 | Cobalt ferrite | C16-phosphate | none | none | none | paraffin | 1 | 16.53 | 21.80 |
| CoFe8H | NFeCocont-04B9 | Cobalt ferrite | C16-hydroxyam. | none | none | none | CHCl3 | 0.5 | 13.80 | 25.20 |
| Fe70.AK.1 | FE70 | Magnetite | C16-phosphate | none | none | none | hexane | 1.5 | 1.03 | 2.07 |
| Fe70.AK.1 | FE70 | Magnetite | C16-phosphate | none | none | none | paraffin | 1.5 | 1.03 | 0.20 |
| NBR1 | CoFe38H | Cobalt ferrite | NHOHCOC12—COOR | PLGA | BSA | none | Water | 0.20 | 10.47 | 10.00 |
| NBR2 | CoFe38H | Cobalt ferrite | NHOHCOC12—COOR | Pluronic | none | none | Water | 0.35 | 10.47 | 10.00 |
| NBR3 | Fe77 | Magnetite | none | BAC-EDDA polymer | none | none | Water | 0.51 | 5.05 | 4.51 |
| NBRF1 | CoFe38H | Cobalt ferrite | NHOHCOC12—COOR | PLGA | BSA | Paclitaxel | Water | 0.20 | 10.47 | 9.50 |
| NBRF2 | CoFe38H | Cobalt ferrite | NHOHCOC12—COOR | PLGA | BSA | 9-nitro Camptothecin | Water | 0.26 | 10.47 | 9.23 |
| NBRF3 | CoFe38H | Cobalt ferrite | NHOHCOC12—COOR | PLGA | BSA | Cis-Diammine platinum (II) dichloride | Water | 0.52 | 10.47 | 10.00 |
| NBRF4 | CoFe38H | Cobalt ferrite | NHOHCOC12—COOR | Pluronic | none | Paclitaxel | Water | 0.31 | 10.47 | 10.00 |
| NBRF5 | Fe77 | Magnetite | none | BAC-EDDA polymer | none | Cis-Diammine platinum (II) dichloride | Water | 0.36 | 5.05 | 3.89 |

All the measurments have been carried out with irradiation at 170 KHz and with a magnetic field of 21 KA/m$^2$ for 30 seconds

The invention claimed is:

1. A hyperthermically effective composition, the composition comprising:
   magnetic nanoparticles functionalised with ethyl-12-(hydroxyamino)-12-oxododecanoate, a polymer optionally containing a pharmacologically active molecule, and an external protecting layer of surface agents wherein said pharmacologically active molecule is chosen among: antitumour agents, antimicrobial agents, anti-inflammatory agents, immunomodulators, molecules acting on the central nervous system or those capable of marking the cells so as to allow their identification with the normal means of diagnostic detection.

2. The composition according to claim 1 wherein said pharmacological active molecule is connected to the polymer or dispersed in it.

3. The composition according to claim 1 wherein said magnetic nanoparticles are spinels and oxides of the $M^{II}M^{III}_2O_4$ type, in which $M^{II}$ is selected from the group consisting of Fe, Co, Ni, Zn, and Mn, and $M^{III}$ is selected from the group consisting of: Fe and Cr a nanometric form.

4. The composition according to claim 3 wherein said magnetic nanoparticles are selected from the group consisting of cobalt ferrite, magnetite and maghemite.

5. The composition according to claim 1 wherein said polymer is a water insoluble polymer selected from the group consisting of polyesters, polyamides, polyanhydrides, polyorthoesters, peptides, polyamineamides, and insoluble organic molecules.

6. The composition according to claim 1 wherein said surface agents are selected from the group consisting of polyelectrolytes, polypeptides, water-soluble proteins, block copolymers, modified polyethylene glycols, modified polysaccharides, phospholipids, polyamineamides, globular proteins, human serum proteins, and pluronics block copolymers.

7. The composition according to claim 1 wherein the composition has an average diameter in the range between 50 and 300 nm.

8. The composition according to claim 7, wherein the magnetic nanoparticles comprise cobalt ferrite.

9. The composition according to claim 1 wherein the composition has an average diameter in the range between 30 and 100 nm.

10. The composition according to claim 1 wherein said magnetic nanoparticle comprises cobalt ferrite, and said polymer is a block polymer.

11. A hyperthermically effective composition, the composition comprising:
magnetic nanoparticles functionalised with a bifunctional compound, and a polymer optionally containing a pharmacologically active molecule wherein the bifunctional compound is ethyl-12-(hydroxyamino)-12-oxododecanoate.

12. The composition according to claim 11 wherein said pharmacological active molecule is connected to the polymer or dispersed in it.

13. The composition according to claim 11 wherein said magnetic nanoparticles are spinels and oxides of the $M^{II}M^{III}_2O_4$ type, in which $M^{II}$ is selected from the group consisting of Fe, Co, Ni, Zn, and Mn, and $M^{III}$ is selected from the group consisting of Fe and Cr a nanometric form.

14. The composition according to claim 11 wherein said magnetic nanoparticles are selected from the group consisting of cobalt ferrite, magnetite and maghemite.

15. The composition according to claim 11 further comprising surface agents selected from the group consisting of polyelectrolytes, polypeptides, water-soluble proteins, block copolymers, modified polyethylene glycols, modified polysaccharides, phospholipids, polyamineamides, globular proteins, human serum proteins, and pluronics block copolymers.

16. The composition according to claim 11 wherein said pharmacologically active molecule is selected from the group consisting of antitumour agents, antimicrobial agents, anti-inflammatory agents, immunomodulators, molecules acting on the central nervous system, and those capable of marking the cells to allow their identification using diagnostic detection methods.

17. The composition according to claim 11 wherein the composition has an average diameter in the range between 50 and 300 nm.

18. The composition according to claim 11 wherein the composition has an average diameter in the range between 30 and 100 nm.

19. The composition according to claim 11 wherein the magnetic nanoparticles comprise cobalt ferrite.

* * * * *